United States Patent
Feygin et al.

(10) Patent No.: US 7,028,726 B2
(45) Date of Patent: Apr. 18, 2006

(54) ROTARY-DRIVE DISPENSER

(75) Inventors: Ilya Feygin, Mountainside, NJ (US); John M. Newsam, San Diego, CA (US)

(73) Assignee: fqubed, San Diego, CA (US)

( * ) Notice: Subject to any disclaimer, the term of this patent is extended or adjusted under 35 U.S.C. 154(b) by 0 days.

(21) Appl. No.: 10/761,681

(22) Filed: Jan. 21, 2004

(65) Prior Publication Data
US 2004/0149776 A1    Aug. 5, 2004

Related U.S. Application Data

(60) Provisional application No. 60/441,757, filed on Jan. 21, 2003.

(51) Int. Cl.
*B65B 1/04* (2006.01)

(52) U.S. Cl. ........................ 141/144; 141/130
(58) Field of Classification Search .................. 141/9, 141/104, 129, 144, 284, 387, 83, 130
See application file for complete search history.

(56) References Cited

U.S. PATENT DOCUMENTS

| | | | | |
|---|---|---|---|---|
| 4,415,011 A | * | 11/1983 | Grant | 141/284 |
| 4,966,205 A | * | 10/1990 | Tanaka | 141/9 |
| 6,457,496 B1 | * | 10/2002 | Chuang | 141/83 |
| 6,772,806 B1 | * | 8/2004 | De Villele | 141/144 |

* cited by examiner

Primary Examiner—Steven O. Douglas
(74) Attorney, Agent, or Firm—DeMont & Breyer, LLC

(57) ABSTRACT

A liquid dispenser that uses rotary motion to create a relative movement between one or more dispensing elements and one or more receivers is disclosed. The dispensing elements are fluidically coupled to one or more reservoirs, which contain ingredients that are to be dispensed by the dispensing elements into one or more receivers. The receivers are disposed on a receiver support structure that is located beneath the dispensing elements. In some embodiments, the dispenser operates according to a quasi-continuous dispensing protocol or quasi-simultaneous dispensing protocol, or both quasi-continuous and quasi-simultaneous dispensing protocol.

26 Claims, 11 Drawing Sheets

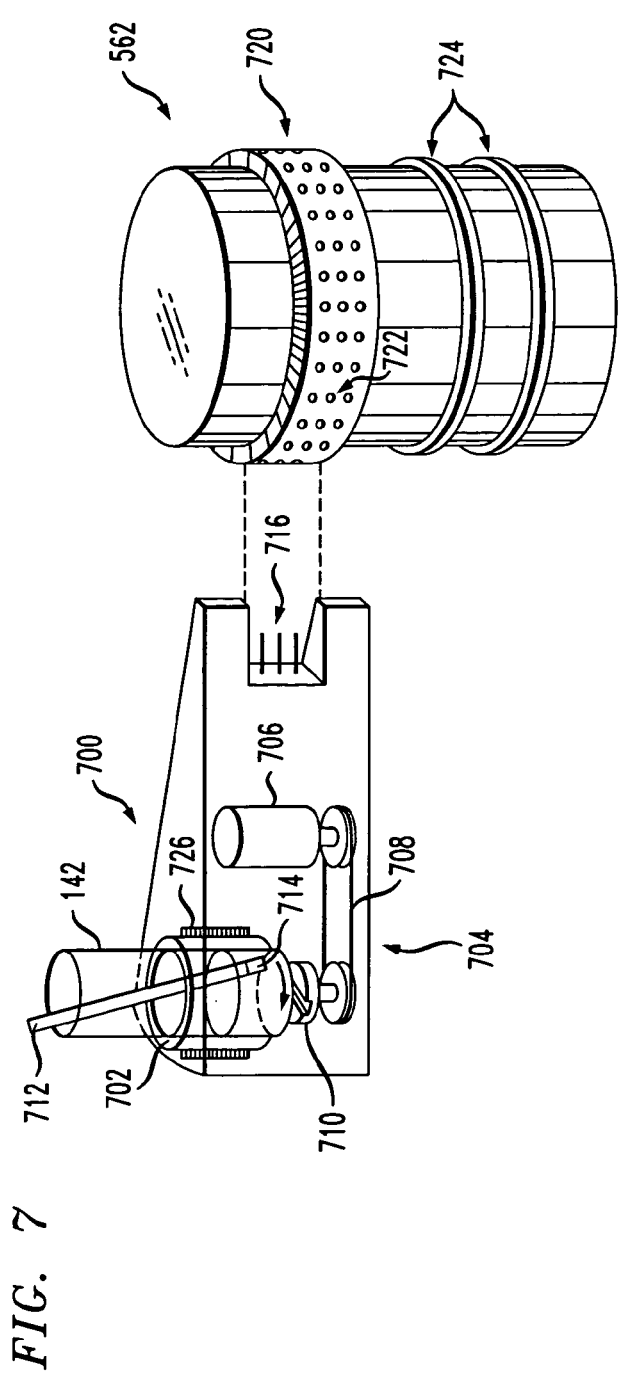
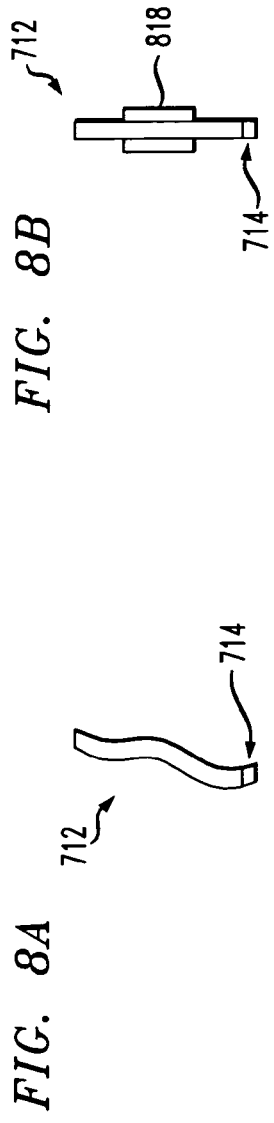
FIG. 7
FIG. 8A
FIG. 8B

ROTARY-DRIVE DISPENSER

STATEMENT OF RELATED CASES

This case claims priority of U.S. Provisional Patent Application Ser. No. 60/441,757, filed Jan. 21, 2003, and incorporated by reference herein.

FIELD OF THE INVENTION

The present invention relates generally to liquid dispensers, and more particularly to a liquid dispenser that is capable of controllably dispensing a plurality of liquids into a plurality of receivers.

BACKGROUND OF THE INVENTION

A variety of industrial and research applications require that ingredients, typically liquid, be dispensed into vessels or other types of receivers. Representative applications include formulation chemistry, mixing of dyes, pharmaceuticals, clinical research, genetic research, and combinatorial chemistry, to name a few.

It is desirable for a dispenser that is intended for these applications to be capable of:
  dispensing one or more liquid ingredients into one or more receivers;
  dispensing very small quantities of liquid (e.g., nano-liter to micro-liters);
  dispensing liquid ingredients rapidly and accurately; and
  monitoring the dispensing operation with real-time analysis and feedback.

But few if any are. Rotary-type dispensers, wherein the dispensing elements or the receivers are moved in circular fashion, are well suited, at least in concept, to dispensing one or more ingredients onto or into one or more receivers. In fact, several prior-art dispensers have been developed that use rotary motion in conjunction with a dispensing operation.

U.S. Pat. No. 6,192,945 B1 to Ford et al. discloses a fluid dispenser for an automated biological reaction system. The dispenser includes a circular reagent tray that supports reagent fluid dispensers. The reagent tray rotates to successively position individual fluid dispensers into a reagent delivery position over a slide. Once positioned, reagent is dispensed onto the slide and then a subsequent fluid dispenser is rotated into position.

U.S. Pat. No. 6,202,895 B1 to Fox discloses an apparatus for dispensing cosmetic foundation compositions. The apparatus includes a manually-rotatable carousel that receives a plurality of plunger-type dispensing elements. Various reagents (e.g., hair coloring, etc.) are stored in the dispensing elements. In use, the carousel is rotated to position a particular dispensing element over a mixing container. A desired amount of reagent is next dispensed into the mixing container. The carousel is then rotated to position another dispensing element over the mixing container, and so forth.

U.S. Pat. No. 6,338,820 B1 to Hubbard et al. discloses an apparatus for performing assays at reaction sites. The apparatus includes a rotatable substrate having radially-arrayed reaction sites. The apparatus further includes a rotary stepper motor that controllably rotates the substrate. The apparatus also has a dual-function head that includes a fluid dispenser for delivering fluid to a reaction site, as well as a sensor for receiving a signal from the reaction site. The dual-function head is suspended for linear movement across the rotatable substrate.

While illustrative of the manner in which rotary motion can be used in conjunction with a dispensing operation, the dispensers mentioned above are not capable of rapidly and accurately dispensing a plurality of ingredients into a plurality of receivers to create a plurality of formulations. In fact, few if any prior art dispensers, rotary or otherwise, are capable of providing this capability. Furthermore, it is very difficult to accurately dispense very small quantities of liquid or to monitor and correct the dispensing operation in real time.

SUMMARY OF THE INVENTION

A liquid dispenser that uses rotary motion to provide a capability for rapid and accurate dispensing of one or more ingredients into one or more receivers is disclosed.

Functionally, the dispenser includes a drive system, a dispensing system, and a system controller. The drive system creates a relative motion between dispensing elements (e.g., nozzles, etc.) and underlying receivers (e.g., vials, etc.) so that they align on a continuing basis. Fluid is dispensed from the dispensing elements into the receivers. The system controller coordinates the operation of the drive system and the dispensing system.

The dispenser can be configured in various ways. In one configuration, the dispensing elements are moved by the drive system to align with stationary receivers. In an illustrative embodiment of this configuration, the dispenser includes at least one arm that is coupled to a drive shaft. The arm has at least one dispensing element, which is coupled to one or more reservoirs. The reservoirs contain the bx;1ingredient(s) that are to be dispensed by the dispensing elements. The reservoirs are disposed on a reservoir support structure, which, like the rotatable arm, is coupled to the drive shaft.

A drive element rotates the drive shaft, causing both the arm and the reservoir support structure to rotate. Under the control of the system controller, the dispensing elements deliver liquid ingredients into one or more receivers. The receivers are disposed on a receiver support structure that is located between the dispensing elements and the reservoir support structure.

In another configuration, the receiver support structure, and the receivers along with it, are moved by the drive system to align with stationary dispensing elements. In an illustrative embodiment of this configuration, the dispenser has coaxial shafts: an inner shaft, which does not rotate, and an outer shaft, which does. At least one arm having at least one dispensing element is attached to the top of the non-rotating inner shaft. The dispensing elements are coupled to one or more ingredient-containing reservoirs. A receiver support structure is coupled to the rotatable outer shaft. As the shaft is rotated, the receiver support structure and the receivers move beneath dispensing elements to receive liquid.

In yet another configuration, the dispenser is capable of moving either the dispensing elements to stationary receivers or, in another mode of operation, moving the receivers to stationary dispensing elements.

In some variations of any of the configurations summarized above, the receiver support structure is a platform that comprises a plurality of pie-shape segments. Each segment, which is advantageously independently removable from the platform, includes an opening that is sized to accommodate a receiver. In some additional variations, each segment includes a stirrer motor that drives a magnet, which, in turn, drives a stirrer that is disposed in the receiver. Additionally, each segment can be provided with heating and cooling capabilities.

In additional variations of the present dispenser, each receiver includes one or more sample ports through which liquid is withdrawn from and returned to the receiver. This withdrawal and return process creates mixing or emulsification action within the receiver. In yet further variations, each receiver is coupled to a respective analysis window, which receives liquid from the receiver. The analysis window is configured to be used in conjunction with one or more analytical stations. The analytical stations are capable of providing analyses of the liquid that is retained within the analysis window. Some of the analyses are advantageously performed in real time, so that the results can be fed back to the system controller to make corrections to the dispensing operation.

The system controller implements and coordinates the activities of dispensing system and drive system in accordance with a dispensing protocol. In accordance with one dispensing protocol, ingredients are incrementally dispensed from the dispensing elements as a series of pulses. In accordance with this dispensing protocol, the various ingredients are added quasi-continuously (i.e., a near-continuous flow of an ingredient) and/or quasi-simultaneously (i.e., all ingredients combined at substantially the same time) to the receivers. See applicant's co-pending patent application entitled "Method and Apparatus for Quasi-Continuous and Quasi-Simultaneous" filed on Jan. 21, 2003 as Ser. No. 10/348,769 and incorporated by reference herein.

When implementing the quasi-continuous dispensing protocol in conjunction with the present dispenser, the dispensing elements (or receivers) are in continuous motion. This provides several benefits and, in fact, solves certain "classic" dispensing problems. In particular, to the extent that the ingredients are dispensed by the present dispenser in accordance with the quasi-continuous dispensing protocol:

- a common manifold error that otherwise arises when a single reservoir feeds multiple arms/dispensing elements is overcome;
- the quantity of liquid delivered to each receiver can be determined to a high degree of accuracy using simple techniques; and
- problems can be rapidly corrected during dispensing operations using real time analysis and feedback.

These and other variations of a dispenser in accordance with the illustrative embodiment of the present invention are illustrated in the Drawings and described further in the Detailed Description section of this specification.

BRIEF DESCRIPTION OF THE DRAWINGS

FIG. 7 depicts a receiver support structure that is has a plurality of individually-removable segments.

FIGS. 8A and 8B depicts a stirrer for use in conjunction with the receivers.

DETAILED DESCRIPTION

Definition of terms and additional considerations:

"Liquid(s)" means material(s) that are liquid at the temperature of operation of the dispenser, materials that are liquefied by various physical processes, liquid suspensions (e.g., material(s) that are suspended in a liquid carrier, etc.), slurries, even solids that have properties that allow them to "flow," (e.g., fluidized solids, etc.). Thus, the term "liquid" includes solids that are "naturally" flowable or rendered flowable using appropriate operations (e.g., processing, etc.) or appropriate conditions (e.g., temperature, etc.), etc.

"Fluid" means gases, vapors, and liquids.

"Coupled" means that (coupled) elements cooperate, communicate, attach to, or otherwise influence or affect one another. For example, fluid can flow between (fluidically) coupled elements (e.g., a reservoir and a dispensing element coupled by a conduit, etc.). Also, a force exerted by or experienced by a first of two (mechanically) coupled elements can affect the second element, whether or not the two elements are directly attached to one another.

Tasks and Subtasks. The operation of the illustrative embodiment is described in terms of tasks and subtasks, rather than steps. This is because, as will be clear to those skilled in the art, some of the described tasks and subtasks can be performed in a single step, while others cannot. Furthermore, the illustrative embodiment is more easily understood when it is described in terms of its constituent tasks and subtasks than if it were described, formalistically, in terms of "steps."

Elements described in terms of their function. Some elements of the illustrative apparatus are described functionally, or in terms of the tasks or subtask that they carry out.

As will be clear to those skilled in the art, these elements can be implemented using shared or dedicated hardware including, for example, hardware capable of executing software, such as a suitably-programmed, general purpose processor.

Figure 1A:
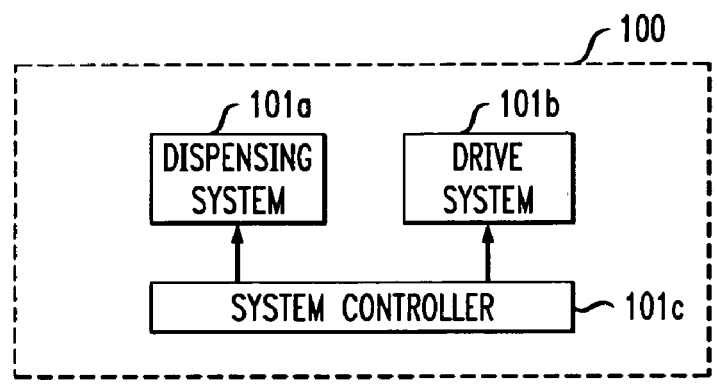
FIG. 1A depicts, via block diagram, basic functional components of a dispenser in accordance with the illustrative embodiment of the present invention.

FIG. 1A depicts a block diagram of the basic functional components of dispenser 100 in accordance with the illustrative embodiment of the present invention. Dispenser 100 comprises dispensing system 101*a*, drive system 101*b*, and system controller 101*c*.

The implementation details of dispensing system 101*a* and drive system 101*b* can vary as a function of which of the element(s)—the dispensing elements (e.g., nozzles, etc.), the receivers (e.g., vessels, etc.), or both—is moved by drive system 101*b*. First, embodiments of dispenser 100 are described wherein the dispenser is configured so that the dispensing elements are moved into alignment with stationary receivers. Next, embodiments of dispenser 100 are described wherein the dispenser is configured so that the receivers are moved into alignment with stationary dispensing elements. Finally, embodiments of dispenser 100 are described wherein the dispenser is configured so that either the dispensing elements or the receivers can be moved (into alignment with the other).

After describing the illustrative embodiments of these three basic configurations of dispenser 100, a description of various features and optional features that can be used with any of the dispenser configurations is provided. Finally, a description of the system controller 101*c* is provided and the operation of dispenser 100 in accordance with a quasi-continuous dispensing protocol is described.

Figure 1C:
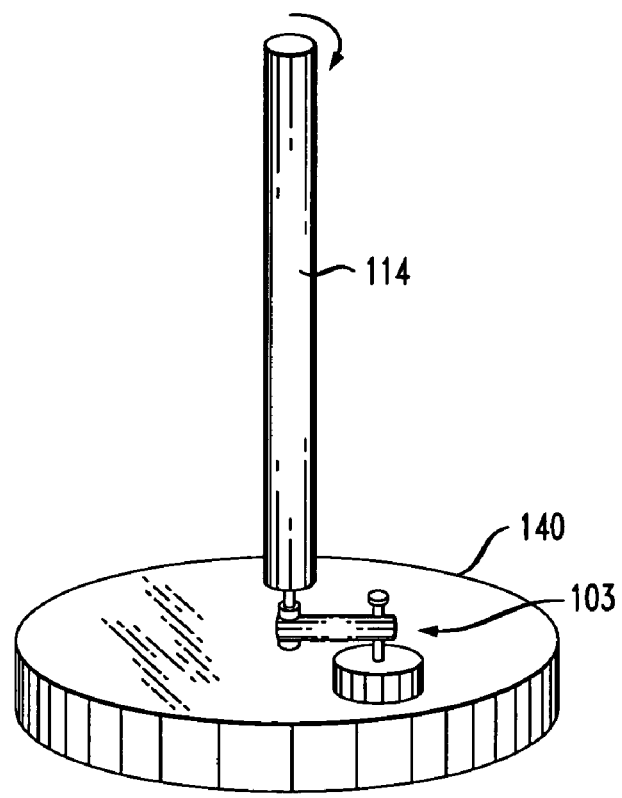
FIG. 1C depicts a drive for driving the drive shaft depicted in FIG. 1B.
Figure 1B:
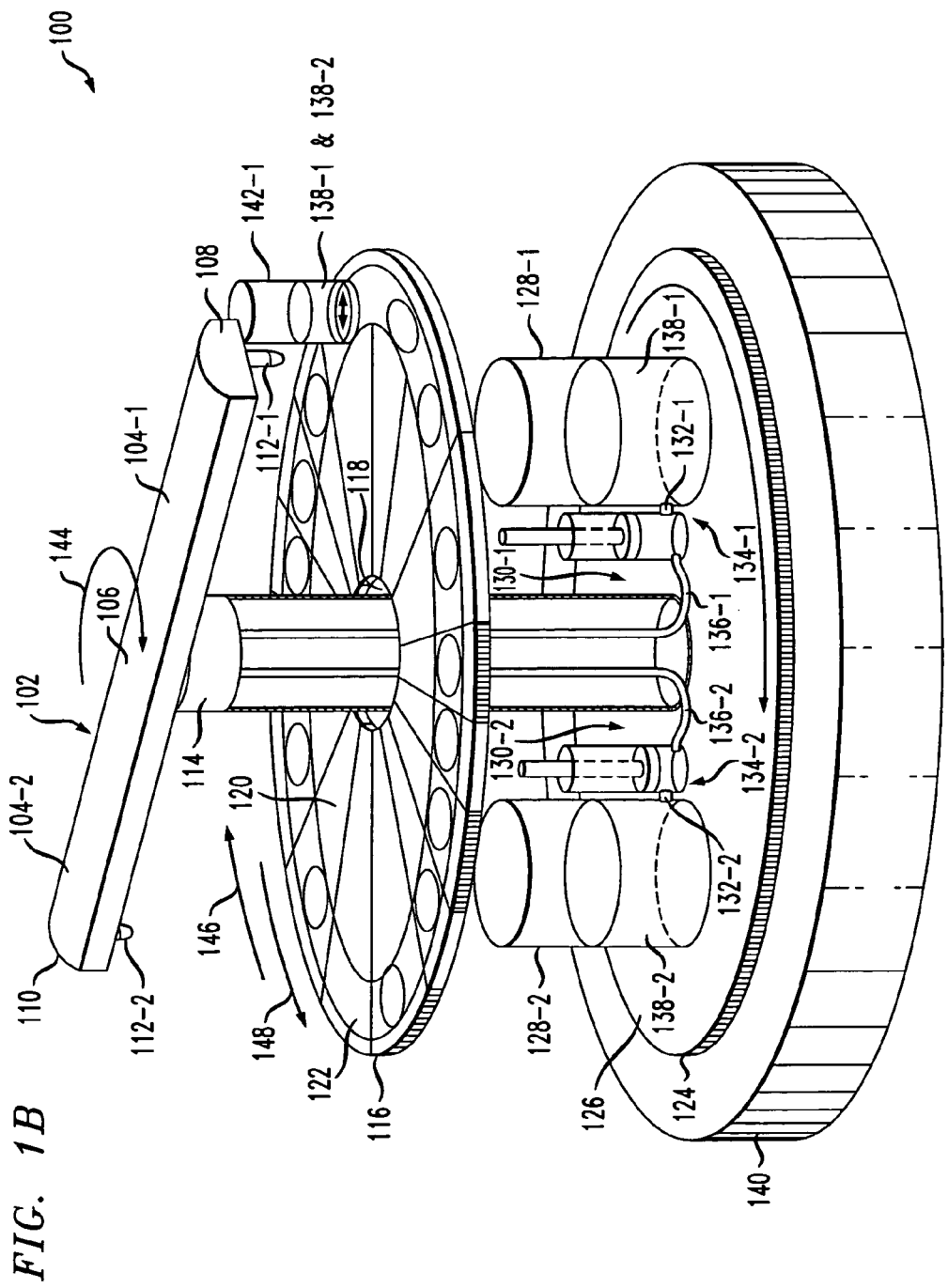
FIG. 1B depicts, via perspective view, a first illustrative embodiment of a dispenser in accordance with the present invention, wherein dispensing elements are moved to bring them into alignment with receivers.

Dispenser 100 Configured to Move the Dispensing Elements into Alignment with Stationary Receivers Referring now to FIG. 1B, dispensing system 101*a* includes reservoir(s) 128-1 and 128-2 (generally "reservoir(s)" 128), liquid-transport system(s) 130-1 and 130-2 (generally, "liquid-transport system(s) 130"), dispensing element(s) 112-1 and 112-2 (generally "dispensing element(s) 112"), and receiver support structure 116.

In the illustrative embodiment, each reservoir 128 is coupled to a respective dispensing element 112 via a respective liquid-transport system 130. As a consequence of this connectivity, liquid ingredients that are stored in reservoirs 128 can be delivered to receivers (e.g., receivers 142-1, etc.) that are disposed on receiver support structure 116.

With reference to FIGS. 1B and 1C, drive system 101*b* includes drive 103, drive shaft 114, reservoir support structure 124, and rotatable member 102. (For clarity, only drive 103 and drive shaft 114 are depicted in FIG. 1C.) The elements of the drive system are coupled in such a way that drive 103 is capable of causing reservoir support structure 124 and rotatable member 102 to rotate. Rotation of rotatable member 102 brings dispensing elements 112 into alignment with underlying receivers 142-1, etc. (into which liquid is dispensed). While drive 103 depicted in FIG. 1C is a belt drive, in some variations, a direct drive arrangement is used.

Position sensor 1372 (see FIG. 13), such as a rotary encoder, is used in conjunction with drive 103 so that system controller 101*c* "knows" the position of each dispensing element 112 relative to receivers 142, to the extent that the dispensing elements have moved. It is within the capabilities of those skilled in the art to select and integrate position sensor 1372 into dispenser 100.

With continuing reference to FIG. 1B, rotatable member 102 includes two arms 104-1 and 104-2 (generally "arm(s) 104"). The rotatable member is coupled, near its mid-point 106, to drive shaft 114. Dispensing element 112-1 depends from arm 104-1 near end 108 and dispensing element 112-2 depends from arm 104-2 near end 110. Further description of dispensing elements 112 is provided later in this specification.

Receiver support structure 116, which is implemented as a "plate" or "platform" (hereinafter referred to as "receiver support platform 116" or simply "platform 116,") is disposed beneath arms 104. Platform 116 "surrounds" drive shaft 114 such that the platform and drive shaft are concentric. To this end, platform 116 has centrally-located opening 118 through which drive shaft 114 passes.

In accordance with this embodiment, platform 116 is not coupled to drive shaft 114. In other words, platform 116 is not movable by the drive shaft. Since, in this embodiment, platform 116 is not coupled to drive shaft 114, it must be supported in some other fashion. For example, in some embodiments, platform 116 is supported by several legs (not depicted for the sake of clarity) that engage its lower surface and are attached to base 140.

Even though, in this embodiment, dispensing elements 112 are moved into alignment with receivers 142 (rather than vice versa), it is nevertheless advantageous to provide platform 116 with an independent rotational capability (as indicated by arrows 146 and 148). As described later in this Specification, this rotational capability enables dispenser 100 to be used in conjunction with an analytical station.

With continuing reference to FIG. 1B, upper surface 120 of platform 116 receives one or more receivers 142 at near-perimeter region 122. Only one such receiver, receiver 142-1, is shown in FIG. 1B for the sake of clarity. The radial position of dispensing elements 112 along arms 104 is such that they overlie near-perimeter region 122. Therefore, to the extent that an arm 104 is angularly aligned with a receiver 142, the dispensing element 112 that depends from that arm overlies the receiver.

Reservoir support structure 124 underlies platform 116. In the illustrative embodiment, reservoir support structure 124 is implemented as a plate or platform, hereinafter referred to as "reservoir support platform 124" or simply "platform 124." Upper surface 126 of platform 124 receives one or more reservoirs 128—two of which (reservoirs 128-1 and 128-2)—are depicted in FIG. 1B. Reservoirs 128 store the ingredients that are to be dispensed by dispensing elements 112. The ingredients are advantageously stored in liquid form in reservoirs 128.

It is understood that platform 116 supports receivers 142 and that platform 124 supports reservoirs 128. This functionality can, of course, be accomplished by structures other than a platform. For example, in some embodiments, the receiver support and/or reservoir support are cage structures that attach, via arms, to drive shaft 114, etc.

In the illustrative embodiment, each reservoir 128 is coupled to one dispensing element 112 via liquid-transport system 130 so that liquid can flow from the reservoir to the dispensing element. In FIG. 1B, for example, reservoir 128-1 is coupled to dispensing element 112-1 via liquid-transport system 130-1 and reservoir 128-2 is coupled to dispensing element 112-2 via liquid-transport system 130-2.

Liquid-transport system 130-1 comprises conduit 132-1 (and a check valve, which is not shown), positive-displacement pump 134-1 and conduit 136-1. Likewise, liquid-transport system 130-2 comprises conduit 132-2 (and a check valve, which is not shown), positive-displacement pump 134-2 and conduit 136-2.

With respect to liquid-transport system 130-1, pump 134-1 takes its suction from reservoir 128-1. When actuated, pump 134-1 draws liquid ingredient 138-1 from reservoir 128-1 through conduit 132-1 and pumps it through conduit 136-1 to dispensing element 112-1. Dispensing element 112-1 then dispenses liquid ingredients 138-1 into an underlying receiver 142. Liquid-transport system 130-2 functions in the same fashion in conjunction with reservoir 128-2 and dispensing element 112-2. Other arrangements for transporting liquid from reservoirs 128 to dispensing elements 112, as will occur to those skilled in the art, can suitably be used.

In some variations of the illustrative embodiment, dispensing elements 112 must be actuated independently of any requirement for actuating liquid-transport system 130. In some other variations, however, dispensing elements 112 do not need to be actuated. That is, when liquid is delivered to a dispensing element, the liquid is dispensed without any need to actuate the dispensing element itself. This is described in further detail later in this Specification.

With regard to pump 134, any of a variety of different types of pumps can suitably be used. One type of pumping system that is particularly well suited for this service is a positive displacement pump. Positive displacement pumps, which are well known in the art, can be microprocessor controlled and use a piston-, roller- or peristaltic-type pumping mechanism. In the illustrative embodiment, pump 134 is depicted as having a piston-type pumping mechanism, a common implementation of which is a syringe.

In some other variations of the illustrative embodiment, liquid-transport system 130 does not use a pump. Rather, in these other variations, reservoir 128 is pressurized, such as by a line that runs from a source of pressurized gas to the reservoir. An in-line control valve is used to regulate pressure. In yet some additional variations, neither a pump nor a source of pressurized gas is used in conjunction with liquid-transport system 130. In those variations, a special nozzle (described later in this Specification) is used that draws liquid from reservoirs 128 by inducing a partial vacuum in the nozzle.

Like rotatable member 102, reservoir support platform 124 is coupled to drive shaft 114. With reference to FIG. 1C, drive shaft 114 is coupled to drive 103, which is disposed within base 140. When actuated, drive 103 (e.g., a motor, turbine, etc.) rotates drive shaft 114, such as in the direction indicated by arrow 144. The drive shaft, in turn, rotates rotatable member 102 and reservoir support platform 124 in the same direction (see, FIG. 1B). The rotatable member and reservoir support platform are advantageously driven at the same rate (or otherwise linked) to ensure that conduits 136 will not twist and fail, as would otherwise occur if there were a relative rotational motion between rotatable member 102 and platform 124. Base 140, which is advantageously weighted or otherwise quite heavy, provides stability when arms 104 and platform 124 are rotating.

In FIG. 1B, dispenser 100 is depicted as having two arms 104, two dispensing elements 112, one receiver 142, and two reservoirs 128. It is to be understood that these details are provided by way of illustration, not limitation. In particular, in a typical application, more than one receiver 142 will be used in conjunction with dispenser 100. For example, as a function of the size of platform 116 and the size of receiver(s) 142, eight, twelve, sixteen, twenty four, or some other number of receivers 142 can suitably be used.

Furthermore, in the illustrative embodiment depicted in FIG. 1B, there are two dispensing elements 112-1 and 112-2 and two reservoirs 128-1 and 128-2. Reservoir 128-1 is coupled to dispensing element 112-1 and reservoir 128-2 is coupled to dispensing element 112-2. In some variations of the illustrative embodiment, a single reservoir 128 is coupled to more than one dispensing element 112 (e.g., reservoir 128-1 to dispensing elements 112-1 and 112-2, etc.). This type of arrangement can be problematic, however, since it presents the problem of "common manifold error" (i.e., common manifolds never deliver identical volumes of liquid to parallel lines or nozzles). This topic is addressed later in this Specification. In some other variations of illustrative dispenser 100, more than one reservoir 128 is coupled to a single dispensing element 112 (e.g., reservoirs 128-1 and 128-2 to dispensing element 112-2, etc.).

In some variations of the illustrative embodiment, a fixed number of reservoirs 128 (e.g., five, etc.) is always present on platform 124. In those variations, if some of the reservoirs are not required, then they are either not coupled to a dispensing element 112 or the associated liquid-transport system 130 is not actuated, etc.

Figure 2A:
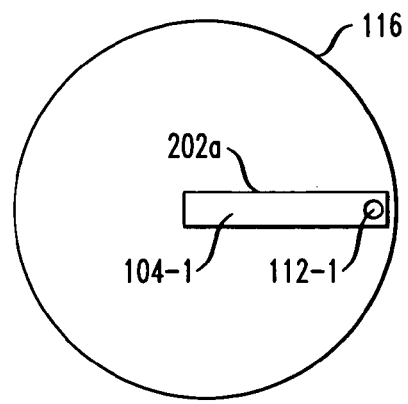
FIGS. 2A, 2B, 2C, 2D, and 2E depict, via top views, several configurations for the rotatable member depicted in FIG. 1B.
Figure 2B:
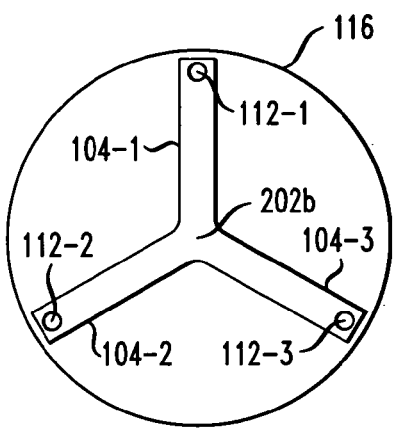
Figure 2C:
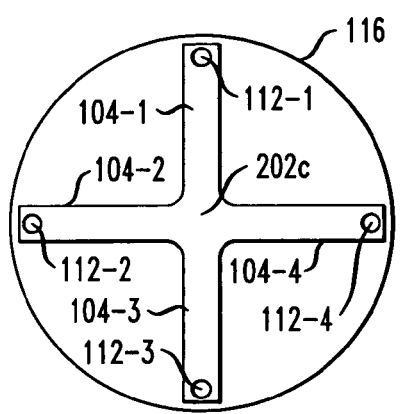
Figure 2D:
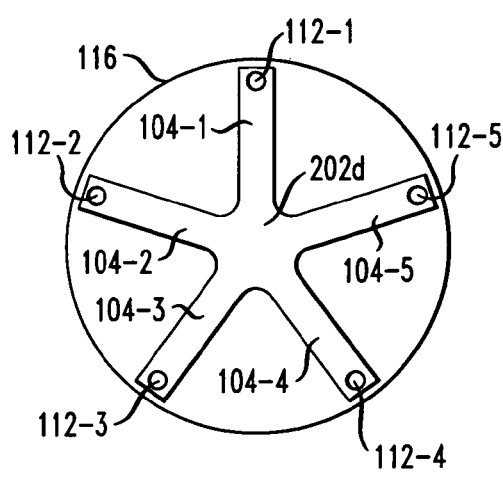
Figure 2E:
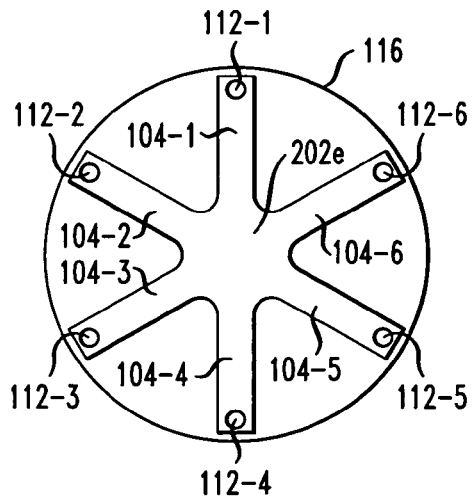

It is to be understood that while rotatable member 102 depicted in FIG. 1B comprises two arms 104-1 and 104-2, in other variations, the rotatable member can have a different number of arms. FIGS. 2A through 2E depicts several such variations of rotatable member 102. In particular, FIG. 2A depicts rotatable member 202a having a single arm 104-1. FIG. 2B depicts rotatable member 202b having three arms 104-1, 104-2, and 104-3. FIG. 2C depicts rotatable member 202c having four arms 104-1, 104-2, 104-3, and 104-4 and FIG. 2D depicts rotatable member 202d having five arms 104-1, 104-2, 104-3, 104-4, and 104-5. And FIG. 2E depicts rotatable member 202e having six arms 104-1, 104-2, 104-3, 104-4, 104-5, and 104-6.

One dispensing element 112 is advantageously disposed toward the end of each arm 104 such that when the arm is angularly aligned with a receiver 142, the dispensing element 112 overlies the receiver. In particular, rotatable member 202a includes dispensing element 112-1, rotatable member 202b includes dispensing elements 112-1, 112-2, and 112-3, rotatable member 202c includes dispensing elements 112-2, 112-2, 112-3, and 112-4, rotatable member 202d includes dispensing elements 112-2, 112-2, 112-3, 112-4, and 112-5 and rotatable member 202e includes dispensing elements 112-2, 112-2, 112-3, 112-4, 112-5, and 112-6.

The position of dispensing elements 112 near the ends of arms 104 is a consequence of situating receivers 142 in near-perimeter region 122. In some other embodiments, receivers 142 are disposed inward of near-perimeter region 122 and, consistent therewith, dispensing elements 112 are disposed inward of the end of arms 104 so that they overlie the receivers. In other words, dispensing elements 112 must be radially aligned with receivers 142.

Using a rotatable element 102, 202 having a relatively greater number of arms 104 offers certain advantages. In particular, a group of receivers 142 can be filled more rapidly if more dispensing elements 112 are used. Also, the use of a relatively greater number of dispensing elements 112 provides an ability to individually dispense a relatively greater number of ingredients. In some variations (not shown) of the illustrative embodiment, at least two dispensing elements 112 are disposed along an arm 104, one inward of the other. Positioning two or more dispensing elements along arm 104 enables the arm to service multiple angularly-aligned receivers that are disposed at different radial locations.

In some variations of dispenser 100, rotatable element 102, 202 is physically adapted to be readily removed from drive shaft 114. This enables rotatable elements 102, 202 to be exchanged, e.g., one having a relatively greater number of dispensing elements 112 for one having a relatively lesser number, etc., as suits the needs of a particular application. In some other applications, dispenser 100 is fitted with a rotatable element 102, 202 that is typically not changed to satisfy application requirements. For example, in some embodiments, dispenser 100 is fitted with rotatable member 202e having six arms 104 and six dispensing elements 112. To the extent that some of dispensing elements 112 are not required for a particular application, they are simply not used (e.g., liquid-transport system 130 for the particular dispensing element 112 is not actuated, etc.).

Figure 3:
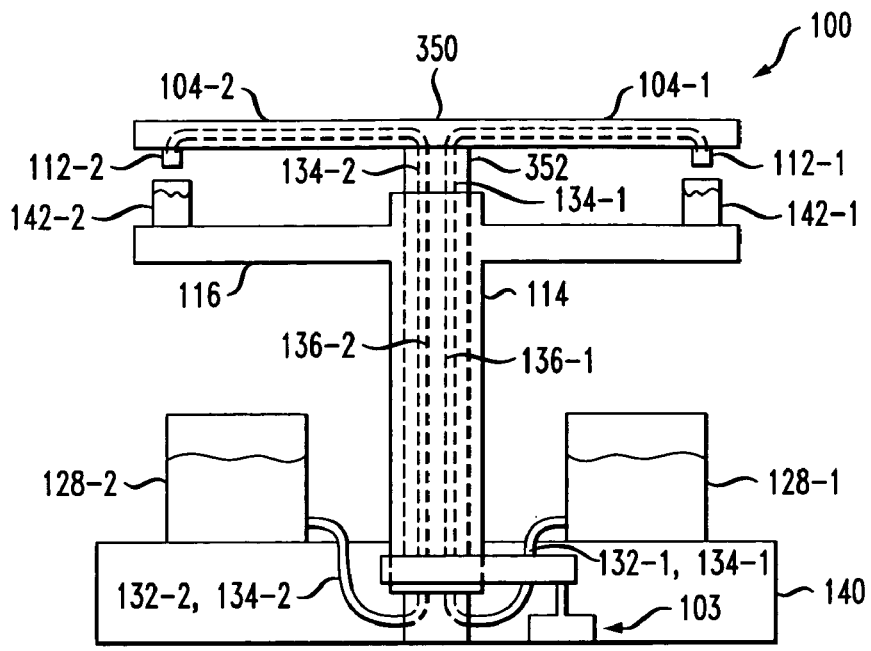
FIG. 3 depicts a side view of a second illustrative embodiment of a dispenser in accordance with the present invention, wherein receivers are moved to bring them into alignment with receivers.
Figure 4:
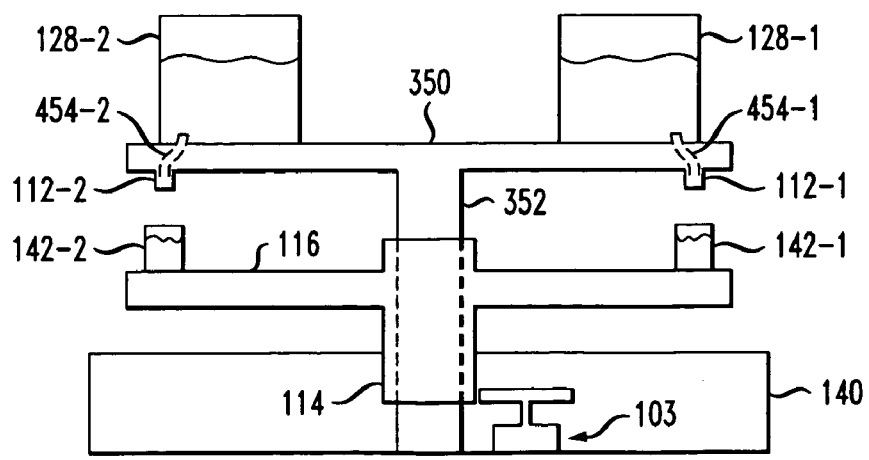
FIG. 4 depicts a side view of a variation of the dispenser depicted in FIG. 3.

Dispenser 100 Configured to Move the Receivers into Alignment with Stationary Dispensing Elements FIGS. 3 and 4 depict illustrative embodiments of dispenser 100 in which the dispenser is configured to move receivers 142 into alignment with stationary dispensing elements 112. Both embodiments use a coaxial arrangement of shafts. In the variation depicted in FIG. 3, non-rotatable member 350 is attached to the top of inner shaft 352. In FIG. 3, non-rotatable member 350 is configured like rotatable member 102 with one or more arms 104-1 and 104-2. Inner shaft 352, which does not rotate, conducts conduits 136-1 and 136-2 to respective arms 104-1 and 104-2. These conduits couple reservoirs 128 to dispensing elements 112.

Outer shaft 114 functions as a drive shaft, and is coupled to drive 103. Receiver support platform 116 is attached to (or integral with) drive shaft 114. When drive 103 is actuated, it turns drive shaft 114, which causes platform 116 to rotate. As platform 116 rotates, receivers 142 move into position beneath dispensing elements 112 to receive liquid. Position sensor 1374 (see FIG. 13), such as a rotary encoder, is used in conjunction with drive 103 so that system controller 101c "knows" the position of each receiver 142 relative to dispensing elements 112, to the extent that platform 116 has moved. It is within the capabilities of those skilled in the art to select and integrate position sensor 1374 into dispenser 100.

Since it is not necessary to rotate reservoirs 128 (unlike embodiments in which arms 104 are rotating) they can be placed directly on base 140. Liquid is conducted from reservoirs 128, through the appropriate conduits, pumps (not shown), etc., and is dispensed through dispensing elements 112.

In dispenser 100 depicted in FIG. 4, reservoirs 128 are disposed on top of non-rotating member 350. In this variation, non-rotating member 350 is configured as a platform so that it can support reservoirs 128. Dispensing elements 112 depend from the underside of non-rotating member 350. Liquid can be gravity fed from reservoirs 128-1 and 128-2, via respective conduits 454-1 and 454-2, to respective dispensing elements 112-1 and 112-2. When actuated, drive 103 causes drive shaft 114 and receiver support platform 116 to rotate.

Dispensing elements 112 that depend from non-movable member 102 can be supplemented, as desired, by additional controlled dispensing elements (not depicted) that are supported by support arms (not depicted) that are attached, for example, to base 140.

Figure 5:
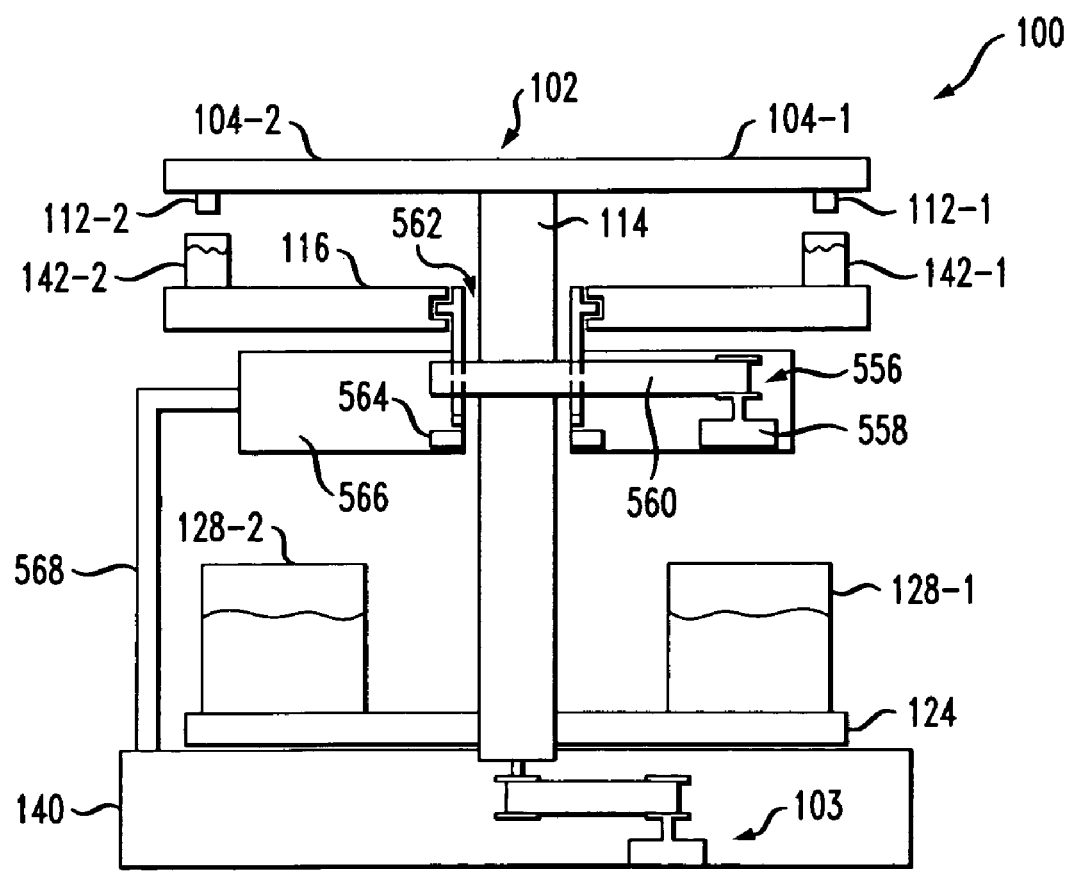
FIG. 5 depicts a side view of a third illustrative embodiment of a dispenser in accordance with the present invention, wherein either the dispensing elements or the receivers are moved.

Dispenser 100 Configured to Move Either the Receivers or the Dispensing Elements FIG. 5 depicts a variation of dispenser 100 wherein receiver support platform 116 on the one hand, and arms 104 and reservoir support platform 124 on the other hand, are capable of rotating independently of each other. In this variation, arms 104 and platform 124 are arranged and driven as depicted in FIG. 1b. Platform 116 is driven by a second drive; in this embodiment: receiver-support drive 556. In the embodiment depicted in FIG. 5, drive 556 comprises motor 558 and belt 560. The belt engages collar 562, which is attached to platform 116. Collar 562 rides on bearing 564. Motor 558 drives belt 560, which, in turn, drives collar 562 and attached platform 116. When a belt-type drive is used, as in the illustrative embodiment, collar 562 advantageously includes belt guides 724 (see FIG. 7).

Drive 556, the lower portion of collar 562, and bearing 564 are disposed in housing 566. The housing is supported by leg 568, which is secured to base 140. Position sensor 1374 (see FIG. 13), such as a rotary encoder, is used in conjunction with drive 556 so that system controller 101c "knows" the position of each receiver 142 relative to dispensing elements 112, to the extent that platform 116 has moved. It is within the capabilities of those skilled in the art to select and integrate position sensor 1374 into dispenser 100.

Dispensing Elements 112

A variety of different types of dispensing elements 112, some of which are depicted in FIGS. 6A through 6E, can be used in conjunction with the various configurations of dispenser 100 that have been described above. The particular type of dispensing element 112 that is used depends, to a certain extent, on the particular type of liquid-transport system 130 being used. For example, when liquid-transport system 130 incorporates a pump, such as a positive-displacement pump, dispensing element 112 can be simply embodied as an orifice, such as the open end 670 of conduit 136 (see, FIG. 1B). The orifice must be appropriately sized so that the liquid can be dispensed as a directed stream. The size of the orifice is a function of pressure/flow rate of the liquid that is being dispensed. When dispensing micro-liter liquid volumes, the size of the orifice is typically in a range of about 0.1 millimeters to 1 millimeter in diameter.

Figure 6A:
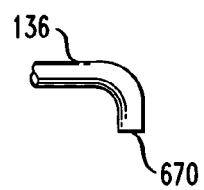
FIGS. 6A, 6B, 6C, 6D, and 6E depict variations of the dispensing element used in a dispenser in accordance with the present invention.
Figure 6B:
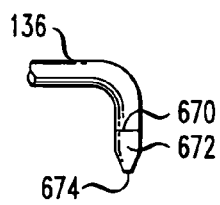

In a further variation of dispensing element 112 that can be used when liquid-transport system 130 includes a pump, dispensing element 112 comprises nozzle 672, which is coupled to end 670 of conduit 136, as depicted in FIG. 6B. The nozzle provides an orifice 674 that can be, for example, smaller in diameter than open end 670 of conduit 136.

Figure 6C:
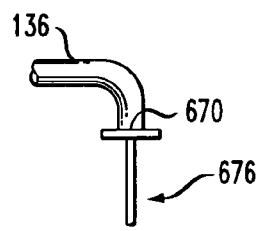

FIG. 6C depicts a further variation of dispensing element 112, wherein dispensing valve 676 is coupled to end 670 of conduit 136. The variation depicted in FIG. 6C can be used whether liquid-transport system 130 incorporates a pump or not (e.g., incorporates a pressurized reservoir instead of a pump, etc.). Suitable dispensing valves 676 are available from a large number of commercial suppliers. Such valves can be designed to handle milliliter, micro-liter or nano-liter volumes of liquid that is delivered in stream, droplet or aerosol patterns. It is understood that when dispensing element 112 is a valve, the valve must be actuated (in addition to any requirement for actuating liquid-transport system 130) to dispense liquid.

Dispensing valve 676 advantageously possesses at least some of the following characteristics:
  very fast (about 1 millisecond response time) and repeatable opening and closing times; and
  has a very low CV (coefficient of variation) of about 5 percent or less; and
  an exit orifice that is shaped and dimensioned to reduce flow turbulence and reduce the incidence of satellite droplets; and
  the valve should have a minimum dead volume and otherwise possess shape and surface characteristics that decrease any tendencies for liquid losses and accumulation; and
  special materials or coatings to improve inertness of internal components and increase life expectancy; and a hard-on-hard valve seat, such as a sapphire to ruby valve seat.

These characteristics are particularly important when a very small volume (e.g., micro-liters or nano-liters) of liquid is being dispensed. A valve that possesses all of these characteristics is commercially available from TechElan of Mountainside, N.J. ("Sub-micro-liter dispensing valve").

Figure 6D:
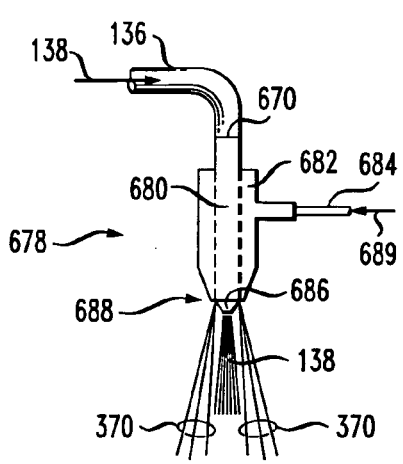

FIG. 6D depicts yet an additional variation of dispensing element 112. The variation depicted in FIG. 6D is a "dual-flow" nozzle 678 that includes inner passageway 680 and surrounding shroud 682. Liquid ingredient 138 is delivered via conduit 136, under the control of an in-line valve (not depicted), to inner passageway 680 and dispensed through orifice 686. An inert, secondary fluid 689 (preferably but not necessarily a gas) is delivered, via conduit 684, to shroud 682 and dispensed through annular opening 688.

Secondary fluid 689, which is controlled independently of ingredient(s) 138, forms a "sheath" that, at suitable rates of flow, reduces the tendency of dispensed liquid to "fan" or spread. The sheath focuses, concentrates or otherwise directs the flow of liquid ingredient 138 toward a receiver. Furthermore, secondary fluid 689 is capable of accelerating the flow of liquid from nozzle 686 to a receiver, thereby speeding the dispensing operation. Additionally, secondary fluid 689 carries (into a receiver) any residual droplet that might otherwise form at orifice 686 at the completion of a dispense.

Figure 6E:
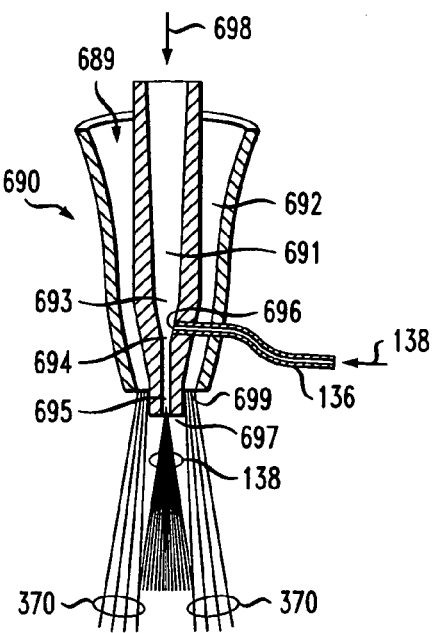

A further variation of dispensing element 112 is depicted in FIG. 6E. The variation depicted in FIG. 6E is a nozzle 690 that is similar to the dual-flow nozzle shown in FIG. 6D in that it includes an inner passageway 691 and a surrounding shroud 692. In the variation that is depicted in FIG. 6E, however, inner passageway 691 is configured in the well-known venturi configuration. In particular, inner passageway 691 includes convergent region 693, throat 694, and divergent region 695. Convergent region 693 typically has an included angle of about 20 degrees and divergent region 695 has an included angle of about 10 degrees.

Carrying fluid 698 (typically, but not necessarily, a gas) flows through inner passageway 691. If ingredient(s) 138 are dispensed pulse-wise (see discussion of quasi-continuous dispensing protocol later in this specification), then the flow of carrying fluid 698 is, more accurately, a pulse of carrying fluid. A pulse of carrying fluid can be generated, for example, using a fast-acting pneumatic valve. Valves suitable for this service are available from FESTO, Inc (Germany) and other suppliers.

The flow of carrying fluid 698 through inner passageway 691 creates low pressure in throat 694. The low pressure in the throat draws in liquid 138 that is "waiting" in conduit 136 (held there by capillary forces). Liquid ingredient 138 enters throat 694 through orifice 696 and is dispensed through orifice 697. As a consequence of the venturi configuration, neither a pump nor a source of pressurized gas for pressurizing reservoir 128 is required as part of liquid-transport system 130.

In some variations, independently-controlled, inert, secondary fluid 689 (preferably but not necessarily a gas) is delivered by a conduit (not shown) to shroud 692 and dispensed through annular opening 699. As described above, secondary fluid 689 forms a "sheath" for focusing, etc., the flow of liquid ingredient 138 from orifice 697. In some embodiments, carrying fluid 698 and secondary fluid 689 are the same fluid.

It is noteworthy that carrying fluid 698 and secondary fluid 689 can reduce contact between the liquid within each receiver 142 and the ambient environment by blanketing each receiver 142. Alternatively, one of dispensing elements 112 can simply be dedicated to dispensing inert gas to blanket receivers 142.

Segmented Receiver Support Platform 116

In some variations of the illustrative embodiment, receiver support platform 116 is composed of a plurality of pie-shaped segments 700, as depicted in FIG. 7. This segmented platform can be used in conjunction with the various configurations of dispenser 100 that have been described above.

Each segment 700 (only one of which is shown for clarity) advantageously includes opening 702 for accommodating receiver 142. Segment 700 also advantageously includes stirrer drive system 704. In the embodiment depicted in FIG. 7, stirrer drive system 704 comprises motor 706, belt 708, and magnet 710. Stirrer 712 having magnetic tip 714 is disposed within receiver 142. Stirrer 712 will move to follow magnet 710 as it is driven by motor 706. Unlike conventional stirrers that normal reside at the bottom of a vessel, stirrer 712 is elongated, like a swizzle stick. For relatively high-aspect ratio (i.e., length to diameter) vessels, the elongated structure of stirrer 712 is expected to be more effective for stirring the contents of receivers 142. Stirrer 712 is advantageously bent, as depicted in FIG. 8A, or has other adaptations for creating turbulence in the liquid contained in receiver 142. For example, stirrer 712 depicted in FIG. 8B has "vanes" 818. The increased turbulence generally results in improved mixing action.

Each segment 700 is advantageously removably attached to collar 562 at region 720. Holes 722 in region 720 receive pins 716 of segments 700 in mating electrical registration. Power is distributed to each segment 700 via this connection. Power is supplied to collar 562 in known fashion, such as by using a slip-ring connector (not depicted). The power that is delivered to segments 700 can be used, for example, to operate stirrer drive 704 and to energize heating or cooling elements 726. The heating/cooling elements 726 can be electrically-based (e.g., resistive, infrared for heating or Peltier for cooling) and advantageously use a thermal conduction means (not shown), such as liquids, springy metal sponges, thermally-conductive beads, and the like to promote heat transfer to or from receiver 142.

The size and shape of segments 700 advantageously vary to accommodate different-size vessels. And to that end, segments 700 are preferably sized as multiples of a minimum segment size. For example, a minimum-size segment can be 15 degrees, with other larger segments as multiples thereof (e.g., 30 degrees, 45 degrees, etc.).

In FIG. 7, segment 700 is depicted as mating with collar 562 at region 720. This collar is used in the embodiment of dispenser 100 that appears in FIG. 5. It will be understood that drive shaft 114 of FIGS. 3 and 4 can be physically adapted (e.g., incorporate region 720, see FIG. 7) for mating with segments 700.

Sampling/Mixing System 925

In some variations of the illustrative embodiment, dispenser 100 includes sampling/mixing system 925, illustrative examples of which are depicted in FIGS. 9A–9C and 10. Using sampling/mixing system 925, a portion of the contents of a receiver 142 can be removed and then returned to the receiver. Each receiver 142 requires its own sampling/mixing system 925.

Figure 9A:
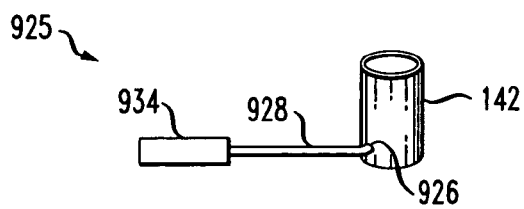
FIGS. 9A, 9B, and 9C depict variations of a system for withdrawing liquid from receivers.
Figure 9B:
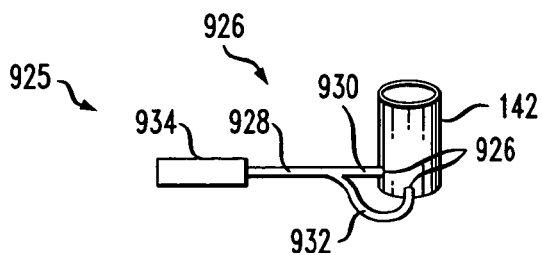
Figure 9C:
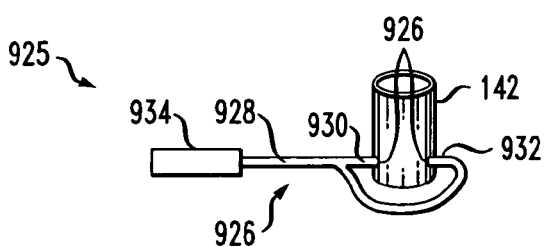

When used with sampling/mixing system 925, receivers 142 are advantageously provided with one or more ports 926, as depicted in FIGS. 9A through 9C. Port(s) 926 connect to conduit 928, which is coupled to aspirator/ dispenser mechanism 934 (e.g., a syringe, bellows, etc.). Aspirator/dispenser mechanism 934 is actuated by actuator 935.

In operation, a sample of liquid is withdrawn from receiver 142 through port(s) 926 and then returned to the receiver through the same port(s) via the action of aspirator/dispenser mechanism 934. This creates a mixing action within receiver 142. When two ports 926 are used, as in depicted in FIGS. 9B and 9C, a capability for intense agitation or emulsification is provided. In FIG. 9B, two ports 926 are oriented at an angle with respect to one another (e.g., between 1 to 179 degrees, etc.), and, in FIG. 9C, the two ports 926 are diametrically opposed (i.e., 180 degrees) thereby generating active, turbulent, counter-flow mixing. End portion 930 of conduit 928 couples to one of the ports, while end portion 932 couples to the other. Liquid that is returned through the two ports co-mingles and emulsifies.

Figure 10:
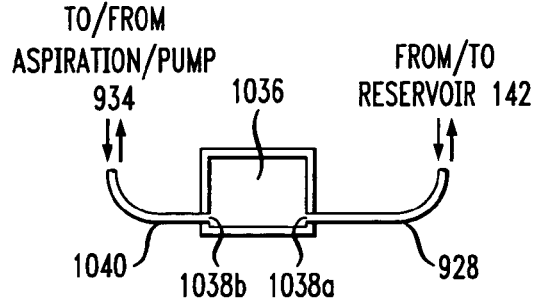
FIG. 10 depicts an analysis window for use in conjunction with the systems depicted in FIGS. 9A–9C.

In some variations, sampling/mixing system 925 incorporates analysis window 1036, depicted in FIG. 10. Analysis window 1036 provides a widened region in which liquid from a reservoir 142 is distributed for optical analysis, such as with analytical station 1142 described below.

As depicted in FIG. 10, conduit 926 couples to port 1038*a* of analysis window 1036. Conduit 1040 is coupled, at one end, to port 1038*b* and at the other end to aspirator/dispenser mechanism 934. Liquid drawn from reservoir 142 by aspirator/dispenser mechanism 934 is distributed throughout analysis window 1036. On the return stroke, etc., of aspirator/dispenser mechanism 934, the liquid within analysis window 1036 is returned to reservoir 142. Analysis window 1036 can be formed, for example, from two, spaced-apart quartz plates that are attached to a frame. The gap between the plates for retaining liquid is in a range of about 1 mm, with a total volume between plates of 5 to 50 micro liters.

Analytical Station 1142

It is often desirable, during the course of dispensing operations, to sample the contents of receivers 142 for compositional analysis. The results of the analysis can be used for a variety of purposes. For example, samples can be taken at regular intervals to monitor reactions and/or obtain kinetic data. Another use for analytical data is to close a control loop that monitors the composition of the mixture or its properties.

Using analytical equipment to monitor formulation operations presents certain challenges or difficulties. One difficulty is that any on-going agitation or heating/cooling processes typically have to be interrupted in order to obtain a sample. Furthermore, if it is desirable to sample plural receivers 142 simultaneously, then each receiver requires an independent analytical system. And if sampling is performed sequentially with a single sampling system, then the system must be cleaned between each sampling operation. A further consideration is that, for many uses of analytical data, the analysis must be performed very rapidly after sampling to be of any value. Consequently, the analytical equipment should be located near to the dispenser. But situating analytical equipment near to the dispenser is not always practical since the typically small amount of available bench-top real estate might be required for other types of equipment.

In some variations of the illustrative embodiment, dispenser 100 incorporates integrated analytical station 1142. One embodiment of integrated analytical station 1142, which addresses the issues described above, is depicted in FIGS. 11 and 12.

Figure 11:
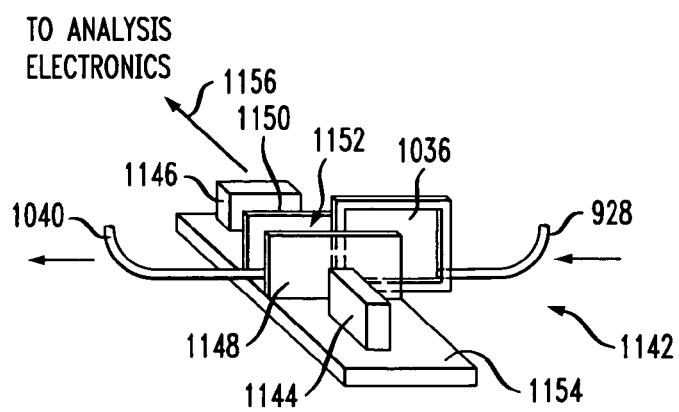
FIG. 11 depicts an analytical station for use in conjunction with the illustrative embodiments of a dispenser in accordance with the present invention.

With reference to FIG. 11, analytical station 1142 includes emitter 1144 and detector 1146. In the illustrative embodiment, optional plates 1148 and 1150 are disposed between the emitter and detector defining a testing region 1152 therebetween. In some embodiments, plates 1148 and 1150 are used as a guide to conduct or route analysis window 1036 into testing region 1152. In such embodiments, plates 1148 and 1150 are advantageously optically transparent (at least at the wavelengths of interest). In some other embodiments, plates 1148 and 1150 provide a filtering function by filtering out certain wavelengths from the radiation that is being delivered by emitter 1144 or that is being received by detector 1146. The various elements (e.g., emitter 1144, etc.) of analytical station 1142 are disposed on support 1154.

In operation, analysis window 1036, containing liquid from reservoir 142, is moved into testing region 1152 between emitter 1144 and detector 1146. Radiation having a wavelength that is appropriate for the analysis being conducted is emitted from emitter 1144. The emitted radiation passes through the liquid sample in analysis window 1036. Radiation that is transmitted through analysis window 1036, or that is generated (e.g., fluorescence, etc.) when the sample is exposed to the radiation, is detected at detector 1146. Signal 1156, which is generated by detector 1146 in response to the received radiation, is received by appropriate analysis electronics (not depicted).

The analysis electronics is capable of processing the signal, in known fashion, for determining certain properties, characteristics, etc., of the sample. Typical analytical tests include spectrophotometry (at wavelengths ranging from ultraviolet to infrared), light scattering detection techniques, differential refractive index detection, capillary-viscometric detection, to name but a few.

Figure 12:
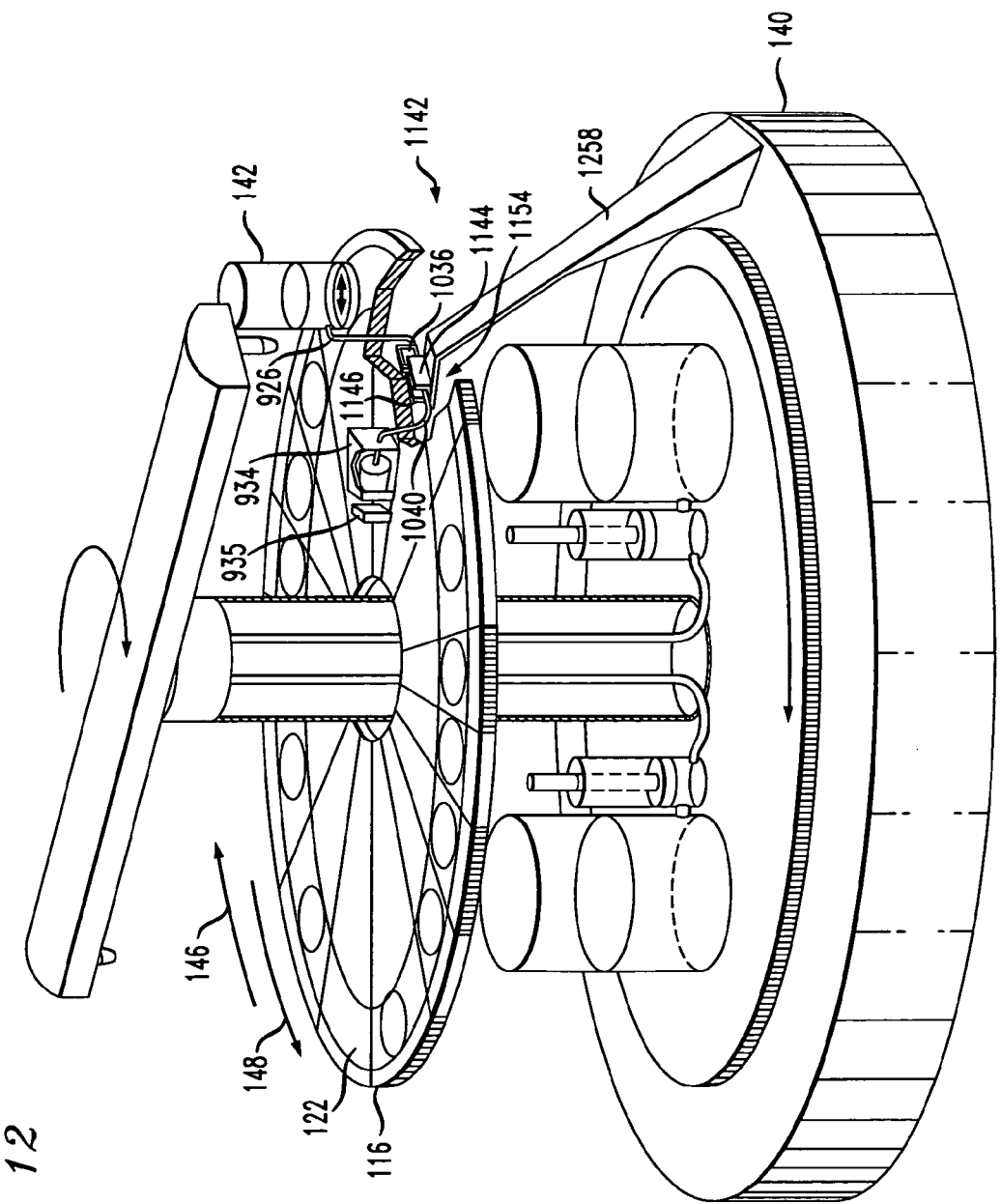
FIG. 12 depicts the analytical station shown in FIG. 11 incorporated into the dispenser depicted in FIG. 1B.

FIG. 12 depicts one way in which analytical station 1142 can be integrated with dispenser 100. In this embodiment, analytical station 1142 is integrated with dispenser 100 having movable arms 104 (see, e.g., FIG. 1B). It is to be understood that analytical station 1142 can be integrated with any of the configurations of dispenser 100 described herein.

As depicted via the "cut-away" view provided in FIG. 12, analytical station 1142 is disposed beneath receiver support platform 116. Analytical station 1142 is supported by support arm 1258, which is attached to base 140. Support arm 1258 suspends analytical station 1142 near the underside of receiver support platform 116 in position to receive analysis window 1036.

To engage analytical station 1142, analysis window 1036 is disposed beneath platform 116. To that end, conduits 926 and 1040 pass through receiver support platform 116.

In operation, liquid is drawn (aspirated) from reservoir 142 into analysis window 1036 by aspirator/dispenser 934 in conjunction with actuator 935. Analysis window 1036 is rotated into position in testing region 1152 (see FIG. 11) by rotating receiver-support platform 116 (i.e., in the illustrative embodiment, receiver-support platform 116 is rotated clockwise in direction 146). To do so, dispenser 100 must incorporate a means for rotating receiver support platform 116, such as receiver support drive 556 (see, FIG. 5 and the accompanying description). For this service, drive 556 operates at slow speed, and, at most, rotates platform 116 about one full revolution. Alternatively, drive 556 can provide discontinuous motion. That is, platform 116 is rotated until analysis window 1036 reaches analytical station 1142 and then stops. This is in contrast to the continuous motion of platform 116 that occurs when operating in accordance with the quasi-continuous dispensing protocol (in configurations of dispenser 100 wherein receivers 142 are rotated). Consequently, a different type of drive 556 might be selected in embodiments in which the drive is used to move receiver support platform 116 for the dispensing operation (and for movement in conjunction with analytical station 1142) as compared to those embodiments in which drive 556 is used only in conjunction with analytical station 1142. In fact, in some embodiments in which receiver support platform 116 is used for both services, two different drives are coupled to platform 116, one for each service. It is within the capabilities of those skilled in the art to select a drive suitable for either one or both of these services.

After the analysis is completed, liquid in analysis window 1036 is pumped, via aspirator/dipsenser 934, back into receiver 142. Analysis window 1036 is rotated out of testing region 1152 and another analysis window that is associated with another receiver 142 is rotated into the testing region.

Although only one analytical station 1142 is depicted in FIG. 12, in some variations, a plurality of analytical stations are integrated with dispenser 100. In some embodiments, each of the analytical stations performs the same test, enabling rapid testing of the samples in the plurality of receivers 142. In some other embodiments, the various analytical stations perform different tests.

System Controller 101c

The operation of dispensing system 101a, drive system 101b, sampling/mixing system 925, and analytical station 1142 are coordinated by system controller 101c. These operations are conducted in accordance with any one of a variety of dispensing protocols (some are described later in this specification), as implemented via system controller 101c.

Figure 13:
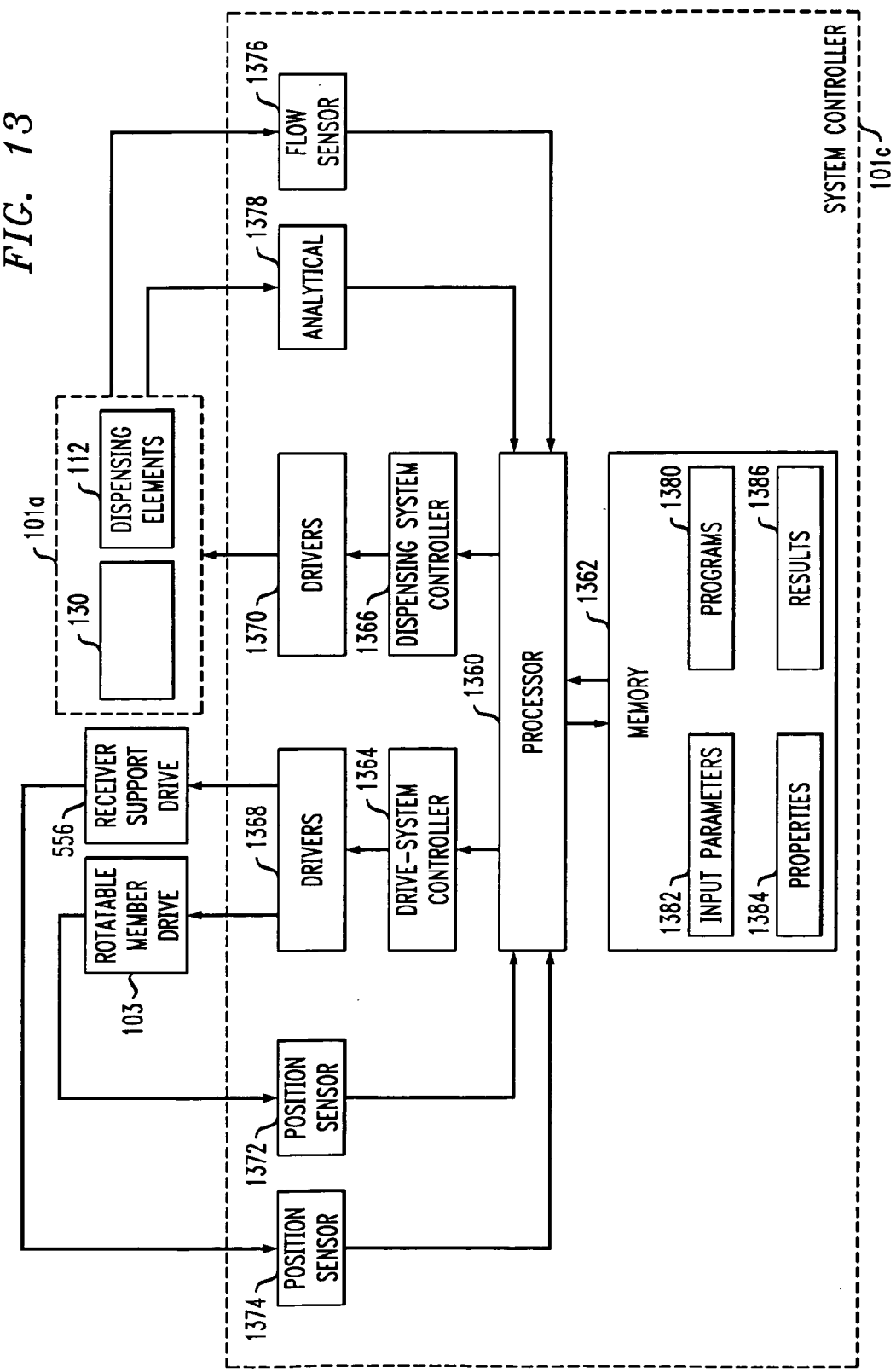
FIG. 13 depicts a simplified block diagram of a control system for use in conjunction with the illustrative embodiments of a dispenser in accordance with the present invention.

FIG. 13 depicts a block diagram of the salient components of system controller 101c. Among other capabilities, the system controller is capable, in some embodiments, of:

causing drive system 101b to create a relative motion between dispensing elements 112 and receivers 142;
causing dispensing system 101a to dispense ingredients;
monitoring the dispensing operation; and
adjusting the dispensing operation.

As will be understood by those skilled in the art, some of the components that compose system controller 101c are implemented using shared or dedicated hardware including, for example, hardware capable of executing software, such as a suitably-programmed, general purpose processor, etc.

In the embodiment depicted in FIG. 13, system controller 101c includes processor 1360, memory 1362, drive-system controller 1364, drive-system drivers 1368, position sensors 1372 and 1374, dispensing-system controller 1366, dispensing-system drivers 1370, flow sensors 1376, and analytical 1378, interrelated as shown.

Processor 1360 is a general-purpose processor that is advantageously capable of performing the tasks described below. In particular, and without limitation, processor 1360 is capable of:

receiving data from a local input device (not shown), such as a keyboard, control panel, touch display, etc., and outputting it to a local output device (not shown), such as a monitor, signaling panel, etc.;
storing parameters that are required to determine the rate at which drive shaft 114 is driven and when and for how long liquid is dispensed into any particular receiver 142, and retrieving those parameters from memory 1362;
executing one or more software programs that are stored in memory 1362;
storing, in memory 1362, the results of any software programs that have been executed; and controlling the operation of drive-system controller 1364 and dispensing-system controller 1366.

Memory 1362 is a non-volatile memory (e.g., an EEPROM, disk drives, an optical device, etc.) for storing:

programs 1380 that are executed by processor 1360;
input parameters 1382 that are required for executing programs 1380;
properties data 1384 (e.g., physical properties/pressure/flow data) for use with some of programs 1380; and
results 1386 that are generated by processor 1360, among other information.

Drive-system controller 1364 converts commands (e.g., move at a certain speed, etc.) that are issued by processor 1360 into drive-(e.g., motor-) control instructions. Drivers 1368 carry out the drive-control instructions thereby causing drive 103 to operate. As a consequence, drive shaft 114 is rotated. In a dispenser that is configured like dispenser 100 depicted in FIG. 1B, rotation of drive shaft 114 causes rotatable member 102 to rotate. In a dispenser that is configured like dispenser 100 depicted in FIG. 3, rotation of drive shaft 114 causes receiver support plate 116 to rotate.

As previously indicated, drive-system controller 1364 moves rotatable member 102 (or receiver support platform 116) so that dispensing elements 112 align, on a continuing basis, with receivers 142. Position sensor(s) 1372 provides positional information to processor 1360 (or drive-system controller 1364 depending upon design specifics) so that the processor "knows" the position of dispensing elements 112 relative to any given receiver 142. In some other embodiments, an encoder (absolute or incremental) is used for the same purpose.

Dispensing-system controller 1366 converts commands (e.g., dispense now, etc.) that are issued by processor 1360 into actuator-(flow-) control instructions. Drivers 1370 carry out the flow-control instructions thereby causing liquid to be dispensed. For example, in the illustrative embodiment depicted in FIG. 1B, controller 1366 and drivers 1370 cause pump(s) 134 to activate and pump liquid from reservoir(s) 128 to dispensing element(s) 112.

Optional flow measurement data, as provided by flow sensor 1376 can be used to close a control loop, so that the flow of ingredients is appropriately adjusted. Obtaining the flow rate of ingredients when dispenser 100 is operating in accordance with the quasi-continuous dispensing protocol is described later in this specification.

Optional analytical measurement data (e.g., composition, etc.), as obtained from analytical 1378 can be fed back to processor 1360 to adjust dispenser operation as appropriate. By way of example, emitter 1144 is advantageously coupled, through appropriate drivers and controllers (not depicted), to processor 1360. The processor coordinates the movement of receiver support platform 116, the actuation of aspirator/pump 934 and the activation of emitter 1090. Similarly, detector 1146 is coupled to processor 1360 so that output signal 1156 (see, FIG. 11) from the detector, or from various analysis electronics (not depicted) that are associated with the detector, is routed to the processor. Processor 1360 uses the results of the analyses to adjust, as required, aspects (e.g., flow rate of a particular ingredient, etc.) of the dispensing operation. To do this, process 1360 sends a signal to dispensing system controller 1366 to take the required action, which, in conjunction with drivers 1370, is carried out.

Those skilled in the art will know how to design and implement the various components and software composing system controller 101c.

Operating Dispenser 100 in Accordance with a Quasi-Continuous Dispensing Protocol Dispenser 100 can be operated in accordance with any of a variety of dispensing protocols, three of which are described below.

In accordance with a first, well-known protocol, the full amount of a first liquid ingredient that is to be dispensed into a first receiver 142-1 is so dispensed, and then the full amount of the first ingredient that is to be dispensed into a second receiver 142-2 is so dispensed. Dispensing of the first ingredient continues, one receiver at a time, until each receiver (that is to receive the first ingredient) receives its portion. Then, the full amount of a second liquid ingredient that is to be dispensed into one or more of the receivers 142 is so dispensed, one receiver at a time. Dispensing continues, one ingredient at a time and one receiver at a time, until all ingredients are dispensed in accordance with the formulation.

In accordance with a second, well-known protocol, the full amount of a first liquid ingredient and the full amount of a second liquid that are to be dispensed into a first receiver 142-1 are so dispensed, simultaneously. Simultaneous dispensing, receiver-by-receiver, of the first and second ingredient, in the full amount, continues until each receiver (that is to receive the ingredients) receives its portion.

In these well-known protocols, drive system 101b moves (dispensing elements 112 or receivers 142) in a stepped or discontinuous fashion.

Alternatively, in accordance with a quasi-continuous dispensing protocol, liquid ingredients are dispensed as a plurality of pulses. Each pulse typically contains a small portion of a total quantity of an ingredient to be delivered to a receiver. For some formulation applications, each pulse contains an amount of ingredient within a range of between ten percent to about twenty percent of the total amount of the ingredient to be delivered to any one receiver 142. Representative applications include those wherein the full quantity of the required ingredients must be delivered very rapidly to receivers 142.

For most formulation applications, each pulse contains an amount of ingredient that falls into one of two ranges. In a first range, each pulse contains an amount of ingredient within a range of about one percent to about ten percent of the total amount of the ingredient to be dispensed to any one receiver 142. In the second range, each pulse contains an amount of ingredient within a range of about one-tenth of one percent to about one percent of the total amount of the ingredient to be dispensed to any one receiver 142.

In yet some further formulation applications, each pulse contains less than one-tenth of one percent of the total amount of an ingredient to be delivered to any one receiver 142. Given a total quantity of liquid to be dispensed, the smaller the quantity of the ingredient that is contained in each pulse, the longer it will take to dispense the full quantity of the ingredient.

Furthermore, in accordance with the quasi-continuous dispensing protocol, a single pulse of a first liquid ingredient is received by substantially all receivers before any receiver gets a second pulse of the first liquid. Yet, this second pulse typically occurs within 0.5 to about 5 seconds after the first pulse. Consequently, the first liquid ingredient is dispensed in an almost-continuous (i.e., quasi-continuous) fashion to each receiver.

In some variations of the quasi-continuous dispensing protocol, all receivers get a pulse of all other ingredients that are to be dispensed before any receiver gets a second pulse of the first liquid. Thus, the ingredients are dispensed in an almost-simultaneous (i.e., quasi-simultaneous) fashion on both an intra- and inter-receiver basis. That is, a given receiver receives one pulse of each of the required ingredients at substantially the same time, and the various receivers receive ingredients at substantially the same time. In some variations, of the quasi-continuous dispensing protocol, the dispensing is both quasi-continuous and quasi-simultaneous.

When operating dispenser 100 in accordance with the quasi-continuous dispensing protocol, drive system 101b moves (dispensing elements 112 or receivers 142) in continuous fashion.

The quasi-continuous dispensing protocol has certain benefits or advantages over known dispensing protocols. These benefits, which are summarized below, are described in greater detail in "Method and Apparatus for Quasi-Continuous and Quasi-Simultaneous Dispensing," U.S. patent application Ser. No. 10/348,769.

One benefit of the quasi-continuous dispensing protocol is its ability to serve multiple vessels with one dispensing mechanism per liquid. This increases the reliability of a dispenser that is operating in accordance with the protocol (relative to a combinatorial-type dispensing system).

Another benefit of the quasi-continuous dispensing protocol is an ability to dispense a near-constant proportional addition of multiple liquid ingredients into multiple receivers. This capability is crucial for the preparation of time-based, reactive formulations (e.g., polymer formulations using different monomers and additives, etc.).

When the quasi-continuous dispensing protocol is implemented using rotary-drive dispenser 100, additional benefits or advantages are obtained over other protocols or other types of dispensers.

One such advantage is that the flow rates of individual ingredients, which are quite low, can be determined to a high degree of accuracy. Normally, when dispensing very small amounts of liquid at high speed, it is difficult to accurately determine the rate at which liquid is dispensed. Rather than measuring the flow from each dispensing element, the total or integrated flow of ingredient from each reservoir 128 is measured (to a high degree of accuracy) using trivial methods (e.g., a flow meter, etc.). And, knowing the timing parameters for the delivery of each ingredient into each receiver 142 (i.e., the time duration of a pulse of a particular ingredient into a particular receiver), the flow into each receiver is obtained by a simple apportioning calculation. This statistically-averaged flow (the flow from each dispensing element is not actually measured) provides a very accurate and true "total dispensed volume."

A second advantage of operating dispenser 100 in accordance with the quasi-continuous dispensing protocol is that any operational problems (i.e., clogged nozzle, etc.) will be readily detected as a deviation in expected flow from a reservoir 128. Since ingredients are dispensed pulse-wise in small increments to most or all receivers, no one receiver should be affected to a greater degree than any other receiver by such operational problems.

A third advantage of operating dispenser 100 in accordance with the quasi-continuous dispensing protocol is that operational problems such as a partially occluded nozzle can be readily corrected by simply increasing pulse length or pressure. Since no one receiver will be affected to any greater degree than another receiver, the dispensing operation can continue without endangering the overall formulation and mixing process.

A fourth advantage of operating dispenser 100 in accordance with the quasi-continuous dispensing protocol is that it overcomes the common manifold problem. In particular, to the extent that a single reservoir 128 is feeding two or more dispensing elements 112, any inconsistencies in the amount of ingredient that is delivered to each dispensing element (the amounts will not be equal) will be averaged over all receivers 142. That is, assuming each receiver 142 gets a pulse of a first ingredient from each of two dispensing elements 112, it does not matter that the amounts of the first ingredient delivered from the dispensing elements are not equal.

Rotary-drive dispenser 100, when operating in accordance with the quasi-continuous dispensing protocol, therefore eliminates most of errors in combinatorial formulations or any proportional fillings.

Dispenser 100 operating in accordance with a quasi-continuous dispensing protocol incorporates:

"Means for determining flow rate," which is defined for use in this description and the appended claims as instrumentalities for measuring bulk flow from a reservoir and for apportioning said flow on a per ingredient, per receiver basis. Means for determining flow rate includes, in some embodiments, a flow meter for measuring bulk flow from each reservoir and a processor 1360 running software 1380 for operating in accordance with a quasi-continuous dispensing protocol.

"Means for real-time adjustment of flow rate," which is defined for use in this description and the appended claims as instrumentalities for changing the quantity of an ingredient contained in a pulse. The quantity of an ingredient in a pulse can be changed by changing the length (i.e., time) of a pulse, or the operating pressure. Means for real-time adjustment includes, in some embodiments, processor 1360 running software 1380 for operating in accordance with a quasi-continuous dispensing protocol, dispensing system controller 1366, and drivers 1370.

"Means for distributed dispensing," which overcomes the common manifold problem, is defined for use in this description and the appended claims as follows. Means for distributed dispensing includes processor 1360 running software 1380 for operating in accordance with a quasi-continuous dispensing protocol, and a liquid delivery system that delivers a first pulse of an ingredient to each of a plurality of receivers before delivering a second pulse of the ingredient to any of the receivers.

EXAMPLE I

Tables I and II below provide an illustration of the operation of dispenser 100 depicted in FIG. 1B operating in accordance with a quasi-continuous dispensing protocol. For the illustration, dispenser 100 includes six reservoirs 128-1 through 128-6 (not depicted for clarity) and rotatable member 102 having six arms 104-1 through 104-6 and six dispensing elements 112-1 through 112-6. For this example, only five of the reservoirs (i.e., reservoirs 128-1, 128-2 and 128-4 through 128-6) are dispensing respective ingredients A, B, C, D, and E through five dispensing elements (i.e., dispensing elements 112-1, 112-2 and 112-4 through 112-6). Ingredients are to be dispensed into eight receivers 142-1 through 142-8. See, FIG. 14. The cycle time (i.e., the time it takes for all the receivers to receive a small amount of each of the formulation ingredients via a "pulse" from each dispensing element) is 0.8 seconds. Each of the eight receivers receives the same amount—10 milliliters—of ingredients B, C, D, and E; however, the amount of ingredient A that is dispensed to each of receivers 142-1 through 142-8 is varied. In particular, while receiver 142-1 receives a total of 10 ml of ingredient A, the other receivers receive a reduced amount as follows (in milliliters):

| | Receiver: | | | | | | | |
|---|---|---|---|---|---|---|---|---|
| | 142-1 | 142-2 | 142-3 | 142-4 | 142-5 | 142-6 | 142-7 | 142-8 |
| Quantity: | 10.0 | 9.8 | 9.5 | 9.2 | 9.0 | 8.8 | 8.6 | 8.4 |

In some embodiments, the deficit in total liquid volume that results from the reduction in an ingredient (e.g., ingredient A, etc.) can be compensated for by the addition of an appropriate amount of an inert liquid compound. Alternatively, if the difference in total volume of the various formulations is relatively small, then it is preferable not to add any diluent to compensate for lost volume. Such decisions are best made on a case-by-case basis by those skilled in the art. For the present example, no additional liquid is added.

Thirty minutes is allotted to produce the formulations. Since each dispensing cycle takes 0.8 seconds, a total of: (30×60) seconds×1 cycle per 0.8 seconds=2250 cycles are required.

Assuming that ingredients B, C, D, and E are dispensed in equal (quantity) pulses, each pulse of ingredients B, C, D, and E contains: 10 ml/2250 cycles=4.44 micro-liters of liquid.

As to ingredient A, the quantity of liquid in the pulses varies as a function of which receiver receives the ingredient. Assuming that 2250 equal pulses are delivered to any given receiver, the pulses contain the following quantities (in micro-liters) of ingredient A:

| | Receiver: | | | | | | | |
|---|---|---|---|---|---|---|---|---|
| | 142-1 | 142-2 | 142-3 | 142-4 | 142-5 | 142-6 | 142-7 | 142-8 |
| Quantity: | 4.44 | 4.36 | 4.22 | 4.09 | 4.00 | 3.91 | 3.82 | 3.73 |

Figure 14:
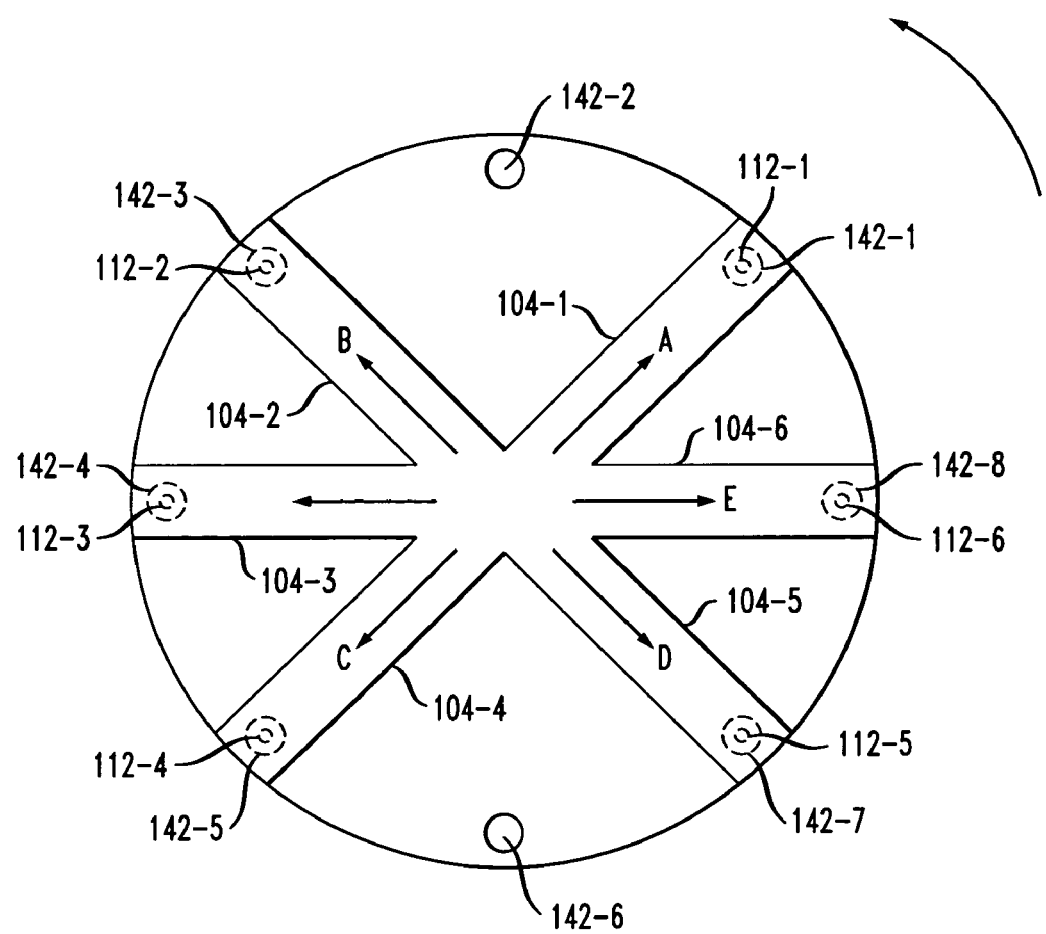
FIG. 14 depicts a top view of the dispenser of FIG. 1 to accompany Example I, providing a "snap shot" of the dispenser at the beginning of a dispensing cycle.

Tables I and II below show the first and second dispensing cycles, respectively, for the Example. FIG. 14 shows dispenser 100 (top view) as each cycle begins ($1^{st}$ pulse), wherein:

dispensing element 112-1 dispenses ingredient A into receiver 142-1;

dispensing element 112-2 dispenses ingredient B into receiver 142-3;

dispensing element 112-3 does not dispense an ingredient (into receiver 142-4);

dispensing element 112-4 dispenses ingredient C into receiver 142-5;

dispensing element 112-5 dispenses ingredient D into receiver 142-7; and dispensing element 112-6 dispenses ingredient E into receiver 142-8.

TABLE I

First Dispensing Cycle—Quantity of Ingredient Dispensed (μl)

| | TIME, sec | | | | | | | |
|---|---|---|---|---|---|---|---|---|
| | 0.0 | 0.1 | 0.2 | 0.3 | 0.4 | 0.5 | 0.6 | 0.7 |
| | | | | RECEIVER | | | | |
| | 1ST PULSE | 2ND PULSE | 3RD PULSE | 4TH PULSE | 5TH PULSE | 6TH PULSE | 7TH PULSE | 8TH PULSE |
| 142-1 | 4.44A | 4.44E | 4.44D | — | 4.44C | — | 4.44B | — |
| 142-2 | — | 4.36A | 4.44E | 4.44D | — | 4.44C | — | 4.44B |
| 142-3 | 4.44B | — | 4.22A | 4.44E | 4.44D | — | 4.44C | — |
| 142-4 | — | 4.44B | — | 4.09A | 4.44E | 4.44D | — | 4.44C |
| 142-5 | 4.44C | — | 4.44B | — | 4.00A | 4.44E | 4.44D | — |
| 142-6 | — | 4.44C | — | 4.44B | — | 3.91A | 4.44E | 4.44D |
| 142-7 | 4.44D | — | 4.44C | — | 4.44B | — | 3.82A | 4.44E |
| 142-8 | 4.44E | 4.44D | — | 4.44C | — | 4.44B | — | 3.73A |

With reference to Table I and FIG. 14, after the first pulse of the first cycle has occurred, 4.44 micro-liters of ingredient A has been dispensed into receiver 142-1, 4.44 micro-liters of ingredient B has been dispensed into receiver 142-3, 4.44 micro-liters of ingredient C has been dispensed into receiver 142-5, 4.44 micro-liters of ingredient D has been dispensed into receiver 142-7, and 4.44 micro-liters of ingredient E has been dispensed into receiver 142-8. During this first pulse, no ingredients are dispensed into receivers 142-2, 142-4, and 142-6, since no dispensing element 112 was near to receivers 142-2 and 142-6 and dispensing element 112-3, which is aligned with 142-2, is not dispensing any ingredient for this particular formulation.

At 0.1 seconds, the second pulse begins. By the time the second pulse begins, the rotatable member 102 has rotated counterclockwise. Dispensing element 112-1 is now in position to dispense ingredient A into receiver 142-2, and so forth. In accordance with the formulation specifics, only 4.36 micro-liters of ingredient A are delivered to receiver 142-2.

After the eighth pulse of the first cycle, 4.44 micro-liters of ingredients B, C, D, and E have been delivered to each of receivers 142-1 through 142-8. And an amount of ingredient A between 4.44 micro-liters (into receiver 142-1) and 3.73 micro-liters (into receiver 142-8) is dispensed into the receivers 142 in accordance with the protocol.

By the end of the seventh pulse (elapsed time of 0.7 seconds), a first pulse of all ingredients A through E are received, for example, by receiver 142-1. This illustrates "quasi-simultaneous" dispensing in accordance with the dispensing protocol. At 0.9 seconds, the first pulse of the second cycle begins, such that about 0.8 seconds elapses between successive deliveries of ingredient A into receiver 142-1. This illustrates "quasi-continuous" flow.

TABLE II

Second Dispensing Cycle—Cumulative Ingredient Dispensed (μl)

| | TIME, sec | | | | | | | |
|---|---|---|---|---|---|---|---|---|
| | 0.8 | 0.9 | 1.0 | 1.1 | 1.2 | 1.3 | 1.4 | 1.5 |
| | | | | RECEIVER | | | | |
| | 1ST PULSE | 2ND PULSE | 3RD PULSE | 4TH PULSE | 5TH PULSE | 6TH PULSE | 7TH PULSE | 8TH PULSE |
| 142-1 | 8.88A | 8.88E | 8.88D | — | 8.88C | — | 8.88B | — |
| 142-2 | — | 8.72A | 8.88E | 8.88D | — | 8.88C | — | 8.88B |
| 142-3 | 8.88B | — | 8.44A | 8.88E | 8.88D | — | 8.88C | — |
| 142-4 | — | 8.88B | — | 8.18A | 8.88E | 8.88D | — | 8.88C |
| 142-5 | 8.88C | — | 8.88B | — | 8.00A | 8.88E | 8.88D | — |
| 142-6 | — | 8.88C | — | 8.88B | — | 7.82A | 8.88E | 8.88D |
| 142-7 | 8.88D | — | 8.88C | — | 8.88B | — | 7.64A | 8.88E |
| 142-8 | 8.88E | 8.88D | — | 8.88C | — | 8.88B | — | 7.46A |

Table II records, on a pulse-by-pulse basis, the accumulation of ingredients in each of receivers 142-1 through 142-8.

From the forgoing, it should be understood that the above-described embodiments are merely illustrative of the present invention and that many variations of the above-described embodiments can be devised by those skilled in the art without departing from the scope of the invention). It is therefore intended that such variations be included within the scope of the following claims and their equivalents.

We claim:
1. An apparatus comprising:
   a receiver support structure, wherein:
      said receiver support structure has a central axis; and
      said receiver support structure supports a plurality of receivers, wherein said plurality of receivers are disposed at a first radial distance from said central axis;
   a first dispensing element, wherein:
      said first dispensing element dispenses a first ingredient; and said first dispensing element is disposed above said receiver support structure at said first radial distance;
a drive system, wherein:
said drive system comprises a first drive; and
said drive system causes, via rotary motion, a relative movement between said dispensing element and said receivers; and
a system controller, wherein:
said system controller comprises means for causing said dispensing element to dispense said first ingredient as a plurality of pulses; and
each pulse contains less than twenty percent of a total amount of said first ingredient to be delivered to one of said receivers.

2. The apparatus of claim 1 wherein each pulse contains less than ten percent of the total amount of said first ingredient to be delivered to said one receiver.

3. The apparatus of claim 1 wherein each pulse contains less than one percent of the total amount of said first ingredient to be delivered to said one receiver.

4. The apparatus of claim 1 wherein each pulse contains less than one-tenth of one percent of the total amount of said first ingredient to be delivered to said one receiver.

5. The apparatus of claim 1 wherein said drive system is rotatably coupled to said first dispensing element.

6. The apparatus of claim 5 wherein said drive system comprises a rotatable member, wherein said rotatable member has at least one arm, and wherein said first dispensing element depends from said arm.

7. The apparatus of claim 6 wherein said drive system comprises a reservoir support structure, wherein said reservoir support structure supports at least a first reservoir.

8. The apparatus of claim 7 wherein said drive system comprises a drive shaft, and wherein:
said rotatable member is coupled to said drive shaft; and
said reservoir support structure is coupled to said drive shaft.

9. The apparatus of claim 8 wherein said drive shaft is hollow, and further comprising:
said first reservoir; and
a first conduit, wherein said first conduit passes through said drive shaft and fluidically couples said first reservoir to said first dispensing element.

10. The apparatus of claim 1 further comprising a second drive, wherein said receiver support structure is rotatably coupled to said second drive.

11. The apparatus of claim 10 wherein said second drive is physically adapted to move said receiver support structure in step-wise fashion.

12. The apparatus of claim 1 wherein said drive system is rotatably coupled to said receiver support structure.

13. The apparatus of claim 12 further comprising:
a non-rotatable member, wherein said first dispensing element depends from said non-rotatable member; and
at least a first reservoir, wherein said first reservoir is disposed on said non-rotatable member.

14. The apparatus of claim 1 wherein said receiver support structure is a platform, wherein said platform comprises a plurality of removable segments, wherein each segment accommodates one of said receivers.

15. The apparatus of claim 14 wherein said removable segments include a stirrer drive.

16. The apparatus of claim 1 wherein said first dispensing element comprises a nozzle, wherein said nozzle has:
an inner passageway leading to an orifice, wherein said inner passageway receives said first ingredient and dispenses it through said orifice; and
a shroud, wherein:
said shroud surrounds said inner passageway;
said shroud receives a first fluid, and
said first fluid controls a flow of said ingredient out of said orifice.

17. The apparatus of claim 16 wherein said inner passageway is characterized by a venturi configuration.

18. The apparatus of claim 1 further said plurality of receivers.

19. The apparatus of claim 18 comprising a sampling/mixing system, wherein, said sampling/mixing system comprises:
a device for aspirating liquid from, and delivering it to, one of said receivers;
a conduit having a first end and a second end, wherein:
said first end is coupled to a port in said one receiver; and
said second end is coupled to said device for aspirating and delivering liquid.

20. The apparatus of claim 19 further comprising an analysis window, wherein:
said analysis window is coupled to said conduit between said first end and said second end; and
said analysis window is disposed beneath said receiver support structure.

21. The apparatus of claim 20 further comprising an analytical station, wherein said analytical station is disposed beneath said receiver support structure, and wherein said analytical station comprises:
an emitter, wherein said emitter emits radiation;
a detector, wherein said detector is coupled to analysis electronics; and
a space between said emitter and said detector, wherein said space defines a testing region and wherein said testing region is physically adapted to receive said analysis window.

22. An apparatus comprising:
a dispensing system, wherein said dispensing system has a first plurality of dispensing elements for dispensing a second plurality of ingredients into a third plurality of receivers;
a drive system, wherein said drive system causes, via a rotary motion, a relative movement between said dispensing system and said receivers to align one of said dispensing elements with one of said receivers; and
a system controller, wherein said system controller comprises:
means for causing said dispensing element to dispense each of said ingredients as a plurality of pulses; and
means for determining flow rate of said second plurality of ingredients into said third plurality of receivers on a per ingredient, per receiver basis, said means for determining flow rate comprising:
a device for measuring total flow of each of said ingredients; and
means for apportioning said flow on a per ingredient, per receiver basis.

23. The apparatus of claim 22 wherein said system controller further comprises means for real-time adjustment of flow rate, wherein said means for real-time adjustment of flow rate comprises means for changing a quantity of ingredient contained in said pulses.

24. An apparatus comprising:
a dispensing system, wherein said dispensing system has a first plurality of dispensing elements for dispensing a second plurality of ingredients into a third plurality of receivers;

a drive system, wherein said drive system causes, via a rotary motion, a relative movement between said dispensing system and said receivers to align one of said dispensing elements with one of said receivers; and a system controller, wherein said system controller comprises means for distributed dispensing.

25. An apparatus comprising:
a first drive;
a rotatable member, wherein:
  said rotatable member is coupled to said first drive; and
  said rotatable member comprises a first arm and a second arm;
a first platform, wherein said first platform:
  is disposed beneath said rotatable member;
  supports a plurality of receivers; and
  is coupled to a second drive;
a second platform, wherein said second platform:
  is disposed beneath said first platform;
  supports a plurality of reservoirs, and
  is coupled to said first drive;
a first dispensing element, wherein said first dispensing element:
  depends from said first arm; and
  is fluidically coupled to at least a first one of said reservoirs; and
a second dispensing element, wherein said second dispensing element:
  depends from said second arm; and
  is fluidically coupled to at a second one of said reservoirs.

26. The apparatus of claim 25 further comprising:
a first liquid-transport system, wherein said first liquid-transport system delivers a first liquid from said first reservoir to said first dispensing element; and
a second liquid-transport system, wherein said second liquid-transport system delivers a second liquid from said second reservoir to said second dispensing element.

* * * * *